United States Patent [19]
Bird et al.

[11] Patent Number: 6,013,861
[45] Date of Patent: Jan. 11, 2000

[54] PLANTS AND PROCESSES FOR OBTAINING THEM

[75] Inventors: Colin R. Bird, Bracknell; Philip A. Fentem, Wokingham, both of United Kingdom; Peter L. Keeling, Ames; George Singletary, Ankenny, both of Iowa

[73] Assignee: Zeneca Limited, London, United Kingdom

[21] Appl. No.: 08/735,491

[22] Filed: Oct. 23, 1996

Related U.S. Application Data

[63] Continuation of application No. 08/562,791, Nov. 27, 1995, abandoned, which is a continuation of application No. 08/394,204, Feb. 24, 1995, abandoned, which is a continuation of application No. 08/199,356, Feb. 18, 1994, Pat. No. 5,522,879, which is a continuation of application No. 07/948,280, Sep. 22, 1992, abandoned, which is a continuation-in-part of application No. 07/899,931, Jun. 17, 1992, abandoned, which is a continuation of application No. 07/528,976, May 25, 1990, abandoned.

[30] Foreign Application Priority Data

May 26, 1989 [GB] United Kingdom ............... 8912165

[51] Int. Cl.$^7$ .......................... C12N 15/00; C12N 15/82; A01H 1/06
[52] U.S. Cl. .................. 800/284; 800/263; 800/320.1; 800/320
[58] Field of Search .................. 435/172.3, 172.1; 47/58, DIG. 1; 800/284, 263, 320.1, 320

[56] References Cited

U.S. PATENT DOCUMENTS

| | | | |
|---|---|---|---|
| 5,004,864 | 4/1991 | Robertson et al. | 800/235 |
| 5,041,378 | 8/1991 | Drummond et al. | 435/234 |
| 5,349,123 | 9/1994 | Shewmaker et al. | 800/205 |

FOREIGN PATENT DOCUMENTS

| | | |
|---|---|---|
| 0372358 | 6/1990 | European Pat. Off. . |
| WO9119806 | 12/1991 | WIPO . |
| WO9211382 | 7/1992 | WIPO . |
| WO9214827 | 9/1992 | WIPO . |
| WO9309237 | 5/1993 | WIPO . |

OTHER PUBLICATIONS

Visser et al, "Inhibition of the expression of the gene for granule–bound starch synthase in potato by anti–sense constructs", Mol. Gen. Genet (1991) 225: 289–296.

Ma et al, "Soluble Starch Synthase From Sweet Corn", Abstract from Supplement to Plant Physiology, vol. 99, No. 1, (131) May 1992.

Fisher et al, "Cloning and Characterization of cDNAs for Starch Branching Enzyme in *Zea MaysI*", Abstract from Supplement to Plant Physiology, vol. 99, No. 1, (519) May/1992.

van der Leij et al, "Expression of the Gene Encoding Granule Bound Starch Synthase After Introduction in an Amylose–Free and a Wildtype Potato (*Isolanum Tuberosum*)", Abstract from Abstracts VIIth Int'l Congress on Plant Tissue and Cell Culture, Amsterdam, (A5–28) Jun./1990.

(List continued on next page.)

*Primary Examiner*—Gary Benzion
*Attorney, Agent, or Firm*—Pillsbury Madison & Sutro LLP

[57] ABSTRACT

Plants, particularly cereal plants, which have improved ability to synthesise starch at elevated or lowered temperatures and/or to synthesise starch with an altered fine structure are produced by inserting into the genome of the plant (i) a gene(s) encoding a form of an enzyme of the starch or glycogen biosynthetic pathway, particularly soluble starch synthase and/or branching enzyme and/or glycogen synthase, which display an activity which continues to increase over a temperature range over which the activity would normally be expected to decrease, and/or (ii) a gene(s) encoding sense and anti-sense constructs of enzymes of the starch biosynthetic pathway, particularly soluble starch synthase and/or branching enzyme and/or glycogen synthase, which alters the natural ratios of expression of the said enzymes or inserts enzymes with special structural characteristics which alter the natural branching pattern in starch.

16 Claims, 26 Drawing Sheets

OTHER PUBLICATIONS

Singletary et al, "Sugar Metabolism in Endosperm of Gene Dose Series Involving Starch Mutants of Maize", Abstract from Plant Physiology, vol. 93, No. 1, (133), May/1990.

Dang et al, "Comparison of soluble starch synthases and branching enzymes from leaves and kernels of normal and amylose–extender maize", Abstract from Biological Abstracts, vol. 89 (48351) 1990.

Napoli et al. (1990) The Plant Cell, p. 279, vol. 2.

van der Krol et al. (1990) Plant Molecular Biology, p. 457, #14.

van der Krol et al. (1990) The PlantCell, p. 291, vol. 2.

Murthy et al. (1986) Biological Abstracts 81(1)139.

Murai et al. (1983) Science, vol. 222, pp. 476–481.

Boyer (1956) Biochem Basis of Plant Breeding, vol. 1, Ed. Xlepa, pp. 139–146.

Salisbury et al. (1985) Plant Physiology, pp. 249, Wadsworth Publishing.

Fig. 18

```
; ID       ECGLGA        standard; DNA; PRO; 1601 BP.
; XX
; AC       J02616;
; XX
; DT       19-APR-1990 (Rel. 23; Last updated; Version 1)
; DT       29-NOV-1987 (Rel. 14; Created)
; XX
; DE       E.Coli glgA gene encoding glycogen synthase, complete cds;  glgC.
; DE       gene encoding glucose-1-phosphate adenylyl transferase, 5'  end.
; XX
; KW       adenylyltransferase;
; KW       ADP-glucose:alpha-1,4-glucan, 4-glucosyltransferase; glgA gene;
; KW       glgC gene; glucose-1-phosphate adenylyl transferase;
; KW       glucosyltransferase; glycogen synthetase; synthetase.
; XX
; OS       Escherichia coli
; OC       Prokaryota; Bacteria; Gracilicutes; Scotobacteria;
; OC       Facultatively anaerobic rods; Enterobacteriaceae; Escherichia.
; XX
; RN       [1]
; RB       1-1601
; RA       Kumar A., Larsen C.E., Preiss J.;
; RT       "Biosynthesis of bacterial glycogen: Primary structure of
; RT       Escherichia coli ADP-glucose:alpha-1,4-glucan,
; RT       4-glucosyltransferase as deduced from the nucleotide sequence of
; RT       the glgA gene";
; RL       J. Biol. Chem. 261:16256-16259(1986).
; XX
; DR       SWISS-PROT; P08323; GLGA$ECOLI.
; XX
; CC       A potential ribosome binding site is located at positions
; CC       1552-1556.
; XX
; FH       Key           Location/Qualifiers
; FH
; FT       CDS           114..1547
; FT                     /note="glycogen synthase (EC 2.4.1.21)
; FT                     /nomgen="glgA""
; FT       CDS           1566..>1601
; FT                     /note="glocose-1-phospate adenylytransferase
; FT                     (EC 2.7.7.27) /nomgen="glgC""
; XX
; SQ       Sequence  1601 BP;  331 A;  405 C;  467 G;  398 T;  0 other;
; CC       Retrieved by M216378 on Mon 18 Nov 91 8:43:12-PDT using FindSeq
ECGLGA
gtgattggtgaaaacgcagaggaagatgcacgtcgtttctatcgttcagaagaaggcatcgtgctggtaa
cgcgcgaaatgctacggaagttagggcataaacaggagcgataatgcaggttttacatgtatgttcagag
atgttcccgctgcttaaaaccggcggtctggctgatgttattggggcattacccgcagcacaaatcgcag
acggcgttgacgctcgcgtactgttgcctgcatttcccgacattcgccgtggcgtgaccgatgcgcaggt
agtatcccgtcgtgatacctccgccggacatatcacgctgttgttcggtcattacaacgggggttggcatt
tacctgattgacgcgccgcatctctatgatcgtccgggaagtccgtatcacgataccaacttatttgtcc
ataccgacaacgtattgcgtttttgcgctgctggggtgggttggggcagaaatggccagcgggcttgaccc
attctggcgtcctgatgtggtgcatgcgcacgactggcatgcaggccttgcgcctgcgtatctggcggcg
cgcgggcgtccggcgaagtcggtgtttactgtgcacaacctagcctatcaaggcatgttttatgcacatc
acatgaatgacatccaattgccatggtcattctttaatattcatgggctggaattcaacggacaaatctc
tttcctgaaggccggtctgtactatgccgatcacattacggcggtcagtccaacctacgctcgcgagatc
accgaaccgcagtttgcctacggtatggaaggtctgttgcaacagcgtcaccgcgaagggcgtctttccg
gcgtaccgaacggcgtggacgagaaaatctggagtccagagacggacttactgttggcctcgcgttacac
ccgcgatacgttggaagataaagcggaaaataagcgccagtcacaaatcgcaatgggatccaaggttgac
gataaagtgccgcttttttgcagtggtgagccgtctgaccagccagaaaggtctcgattcggtgctggaag cctcaccgggttcttcggagcagggcgggcagctggcgctactcggcgcgggcgatccggtgctgcagga
aggtttccttgcggcggcagcggaatacccggtcaggtgggcgttcagattggctatcacgaagcattt
tcgcatcgcattatgggcggcgcggacgtcattctggtgcccagccgtttcgaaccgtgcggcttaacgc
aactttatggatcgaagtacggtacgctgccgttagtgcgacgcaccggtgggcttgctgatacggtttc
tgactgttctctcgagaaccttgcagatggcgtcgccaatgggtttatcttcgaagatagtaatgcctgg
tcgctgttacggactattcgacgtgcttttgtactgtggtcctgtcctccactgtggcggtttgtgcaac
gtcaggctatggcaatggattttggctggcaggtcgcggcgaagtcgtaccgtgagctttactatcgctc
gaaatagttttcaggaaacgcctacatgaatgctccgtttacatattcatcgcccacgcttl
```

PLANTS AND PROCESSES FOR OBTAINING THEM

This is a continuation of application Ser. No. 08/562,791, filed Nov. 27, 1995, abandoned; which was a continuation of application Ser. No. 08/394,204, filed Feb. 24, 1995, abandoned; which was a continuation of application Ser. No. 08/199,356, filed Feb. 18, 1994, now U.S. Pat. No. 5,522,879; which was a continuation of application Ser. No. 07/948,280, filed Sep. 22, 1992, abandoned; which was a continuation in-part of application Ser. No. 07/899,931, filed Jun. 17, 1992, abandoned; and which was a continuation of application Ser. No. 07/528,976, filed May 25, 1990, abandoned.

This invention relates to novel plants having an improved ability to produce starch including an improved ability to produce structurally-altered starch. Such novel plants are capable of producing higher yields than known plants, and/or are capable of producing starch of altered quality. The invention further relates to processes for obtaining such plants.

Temperature is one of the most important ecological factors governing the natural distribution of plants and their satisfactory growth and yield potential in agricultural cultivation. A crop will give its highest yields, and lowest risk of failure, when it is cultivated as close as possible to the specific temperature optima for each of its development stages in the course of the growing season. In many agricultural regions, temperature is not a stable factor for crops with extended growth periods and the plants may suffer stress because of temperatures which are too high or too low, or both, in different intensities and over short or long time intervals.

Many of the world's food crops are cultivated in regions where their yield is constrained by what we have called "thermal thresholds" for optimal growth (Keeling and Greaves, 1990). The actual optimum temperature for maximal yield differs amongst different crops: for example, it is well known that certain cereal plants (such as wheat, barley and maize) give a maximum grain yield at around 25° to 30° C. This optimum temperature is the basis for the calculation of Heat Units (HU) which are used to calculate Growing Degree Units (GDU). GDU is a measure of the HUs a plant requires within a particular temperature range to reach a maximum yield.

"Grain filling" is dry matter accumulation in the grain, and occurs over the period during which the grain increases in weight. Published information on crops such as wheat, barley, maize, rice and sorghum, shows that as the growth temperature increases the duration of grain filling declines. At temperatures below the optimum temperature, the rate of grain filling increases with increasing temperature. This compensates or even overcompensates for reduced duration of grain filling such that, overall, the yield increases with temperature (FIG. 1). However, at higher temperatures the grain filling rate fails to increase further with temperature and, indeed, declines with temperature increases above 30° C. These changes in grain filling rate fail to compensate for further reduction in grain filling duration. The overall effect is reduced yield (and also starch quality) because cereal crops spend significant proportions of time during the grain filling period at temperatures which are higher than optimal for grain filling rate. Thus the limitations on grain filling rate imposes a penalty on the total amount of dry matter that can be accumulated in any one growing season. In addition there is a change in starch fine structure, affecting its quality, because the amylose/amylopectin ratio is affected and the starch granule density is reduced. Although these effects are documented in the literature, their cause has hitherto been unknown.

Arrhenius first developed a generalisation for the effects of temperature on the rates of biochemical reactions and proposed a unifying mechanism involving energy of activation ($E_a$) of chemical reactions. This has become known as the Arrhenius Equation:

$\ln(k_2/k_1) = (E_a/R)(1/T_1 + 1/T_2)$ where the k values represent the velocity constants of each temperature (T) and R is the gas constant. The Arrhenius equation defines a chemical mechanism for the generalisation of a factor "$Q_{10}$" where the rate will double or treble for a 10° C. rise in temperature.

$Q_{10}$=Velocity (T+10)° C./Velocity T° C.

Enzymes, which determine the velocity of any chemical reaction in living organisms, act by lowering the free energy of activation values of the chemical reactions to the extent that the thermal energy which is present in the organism is sufficient to activate the reactants. Thus the $Q_{10}$ values associated with enzyme catalysed reactions are therefore a physical characteristic of the energy of activation achieved by that enzyme. $Q_{10}$ values will therefore remain fixed provided (i) the catalytic site of the enzyme-protein remains functional and (ii) the substrate itself is not affected significantly by changed temperature. It is a well known fact that at temperatures which exceed the thermodynamic stability of proteins (normally considered to be about 40 to 50° C.) the protein structure will "unfold" and its catalytic function will become disrupted and hence it will no longer favour conversion of substrates to products. This phenomenon is well characterised in the literature and has been extensively studied in a variety of living systems as well as in thermophilic organisms. The finding that dry matter accumulation in starch-storing crops apparently has an optimum temperature of 25 to 30° C. is very unusual because this temperature is lower than the temperature at which proteins are normally considered to become disrupted. The phenomenon thus lacks any explanation in the literature.

Our previous studies have led to a new understanding of the metabolic pathway of starch synthesis in developing starch storing tissues (Keeling et al, 1988, Plant Physiology, 87:311–319; Keeling, 1989, ed. C. D. Boyer, J. C. Shannon and R. C. Harrison; pp. 63–78, being a presentation at the 4th Annual Penn State Symposium in Plant Physiology).

We have established that grain filling rate and duration is governed by factors in the grain itself rather than being due to some component of the source tissues. Since starch comprises up to 75% of the grain dry weight in cereals it is logical that the limitation to plant dry matter accumulation referred to above will be most likely due to an effect on starch deposition. This suggests that cereal species or varieties with higher yield will be characterised by either longer duration of starch synthesis in the grain or greater increases in the rate of starch synthesis at elevated temperatures.

Furthermore, this work has given us an understanding of the factors involved in determining the optimum growth temperatures of all starch storing plants, and an understanding of the enzymes responsible for determining the fine structure of starch. In particular, we have investigated the biochemical reactions and interactions between the soluble starch synthase and branching enzymes which contribute to the fine-structure of starch deposition in plants.

An object of the present invention is to provide novel plants having an increased capacity to produce starch and a capacity to produce starch with an altered fine structure.

According to the present invention there is provided a method of producing a plant with altered starch synthesising ability comprising stably incorporating into the genome of a recipient plant one or more than one donor gene specifying an enzyme involved in a starch or glycogen biosynthetic pathway.

The above method is generally applicable to all plants producing or storing starch. The recipient plant may be: a cereal such as maize (corn), wheat, rice, sorghum or barley; a fruit-producing species such as banana, apple, tomato or pear; a root crop such as cassava, potato, yam or turnip; an oilseed crop such as rapeseed, sunflower, oil palm, coconut, linseed or groundnut; a meal crop such as soya, bean or pea; or any other suitable species. Preferably the recipient plant is of the family Gramineae and most preferably of the species *Zea mays*.

The method according to the invention may be used to produce a plant having an improved capacity to produce starch at elevated or lowered temperature. As noted previously, yield increases with temperature until a temperature optimum is reached. Above the temperature optimum, yield begins to decrease. Thus plants growing above (or below) their temperature optimum may not be reaching their full yield potential. Improving the plant's capacity to produce starch at temperatures above or below the temperature optimum will result in increased yield. This may be achieved by increasing the amount or type of starch synthesising enzymes present in the plant. It may also be achieved by altering the actual temperature optimum of starch synthesis to suit the growing conditions of a particular plant. Thus a crop variety may be produced which is adapted to the growth temperature of a particular environment (including particular sites or geographical regions). Normally, it is most useful to improve starch production at temperatures in excess of the normal optimum temperature.

The method according to the invention may also be used to produce a plant having the ability to synthesise starch with an altered fine structure. This may be due to a shift in the temperature optimum of starch synthesis or due to other reasons (such as a change in the overall balance of the different enzymes in the biosynthetic pathway). The fine structure of the starch affects its quality. It is thus possible to generate crops producing starch which is better adapted or targetted to the crops' end-use (such as starch with improved processing properties, improved digestibility, etc).

The method and resulting alterations in starch synthesising ability are particularly advantageous for maize. The temperature optimum of starch synthesis pathway enzyme activity may be matched more closely to the higher temperature ranges encountered in the typical maize growing regions of the world. In addition, the fine structure of the starch may be changed so that novel starches are made in the recipient plant.

The donor gene to be used may be obtained from any biological source which produces starch or glycogen-synthesising enzymes: it may be of plant origin or fungal origin or bacterial origin or animal origin. For example, donor genes may be derived from a plant selected from the following species *Zea mays* (especially the varieties Lima 38, Guanajuato 13, Lima 45, Doebley 479 or teosinte 154), *Zea diploperennis, Zea luxurians, Zea perennis, Zea tripsacum, Zea parviglumis*, and *Zea mexicana*.

Preferably the donor gene specifies soluble starch synthase (E.C. 2.4.1.21) and/or branching enzyme (E.C. 2.4.1.18) and/or glycogen synthase of bacterial origin (E.C. 2.4.1.21) or animal origin (E.C. 2.4.1.11).

We describe the isolation, purification and characterisation of the enzymes soluble starch synthase and branching enzyme and the production of antibodies which can be used in the identification of soluble starch synthase and branching enzyme cDNA clones. we also describe the use of cDNA clones of plant soluble starch synthases (SSS—soluble starch synthase), plant and bacterial branching enzymes (BE—branching enzyme) and plant and animal and bacterial glycogen synthases (GS—glycogen synthase).

The donor gene may be an additional copy of the gene specifying the normal enzyme present in the plant (that is, an additional copy of the wild-type gene). Increased gene expression may also be elicited by introducing multiple copies of enhancer sequences into the 5'-untranscribed region of the donor gene.

The donor gene may specify an alternative enzyme with improved properties compared to those of the normal plant enzyme. For example, glycogen synthase (involved in the glycogen biosynthetic pathway) may be seen as equivalent to soluble starch synthase (in the starch biosynthetic pathway) as it catalyses a similar reaction. However, glycogen synthase (such as glgA found in *E coli*) has a higher temperature optimum of activity than soluble starch synthase, and so its expression in the plant should improve the plant's capacity to produce starch at elevated temperatures. A second example is bacterial branching enzyme (such as glgB from *E coli*) which is equivalent to plant branching enzyme, but may have improved properties.

The donor gene may also specify a modified allelic form of the enzyme with kinetic or allosteric properties different to those of the normal plant enzyme. In particular, the enzyme encoded by the donor gene may have a temperature optimum of activity higher than that of the recipient plant enzyme, or may show enhanced thermal-stability (which may enhance the duration of grain filling).

Expression of improved allelic forms of an enzyme within a recipient plant will produce a plant with increased starch-yielding capacity and/or better starch quality. Examples of such plants include: a plant (especially maize) having a starch synthesising ability which does not decrease with temperature between 25 to 30° C.; a plant (especially maize) containing a soluble starch synthase and/or branching and/or glycogen synthase enzyme with a $Q_{10}$ value greater than 0.8 between 25 and 35° C.; a plant (especially maize) containing a soluble starch synthase and/or branching and/or glycogen synthase enzyme which is resistant to reduction of activity after exposure to a temperature in excess of 40° C. for two hours.

Genes encoding improved allelic forms may be obtained from suitable biological organisms, or endogenous wild-type genes may be manipulated by standard protein or genetic engineering techniques.

Starch-producing and glycogen-producing organisms (including plants, fungi, bacteria, animal cells) may be used as sources of improved enzyme genes. Such organisms may be screened for allelic forms of the enzyme which are more catalytically active than those typically found in the crop. It is also possible to alter the properties of the enzyme in the recipient plant through protein and genetic engineering. Genes encoding variants of the enzymes may be created using molecular techniques or mutagenesis.

The donor gene may be an antisense sequence which reduces expression of the enzyme in the recipient plant. For example, this may be used to alter the balance of the different starch-synthesising enzymes present in the cell which may change the amount or type of starch produced.

In particular, it is possible to insert genes in both sense and/or anti-sense orientations in order to effect a change in the natural ratios of various isoforms of branching enzyme and soluble starch synthase in the recipient plant. Altering the natural ratios of the soluble starch synthase and branching enzyme activities of the recipient plant results in starch being produced with new and novel branching structures, amylose/amylopectin ratios, and an altered starch fine structure.

An antisense donor gene (used to reduce expression of the wild-type gene) may also be incorporated with a sense donor gene encoding a more active replacement enzyme. For example, a sense gene encoding glycogen synthase may be incorporated together with an antisense gene for soluble starch synthase to potentiate the effect of increased temperature optimum described above.

It is possible to insert more than one copy of the donor gene into the recipient genome. Each donor gene may be identical, or a combination of different donor genes may be incorporated. For example, the donor genes may have differing sequences which may encode more than one allelic form of the enzyme or may be derived from more than one source.

In summary, the following are examples of genetic manipulation methods which may be used to produce plants with an altered ability to synthesise starch:

(1) Insertion of an additional copy of the wild-type enzyme gene;

(2) Insertion of a more active or more thermally resistant enzyme gene obtained from a suitable biological organism;

(3) Insertion of multiple copies of the wild-type or enhanced activity enzyme gene;

(4) Modification of the enzyme gene by techniques known in protein engineering to achieve alterations in the kinetics and/or allosterics of the enzyme reaction (eg to achieve thermal stability);

(5) Modification of the promoter sequences using techniques known in protein engineering to achieve enzyme over-expression;

(6) Modification of the sequence of the enzyme gene and/or its promoter and/or the transit peptide.

The said donor gene may be derived from a sexually compatible donor plant and inserted into the recipient plant by sexual crossing of donor and recipient plants.

Alternatively, the donor gene may be isolated from a suitable biological organism, such as a plant, bacterium, fungus or animal cell. Insertion of the donor gene is effected by genetic transformation of the recipient plant. If the donor organism is not sexually compatible with the recipient, the gene to be incorporated into the recipient plant genome is excised from the donor organism and the genome of the recipient plant is transformed therewith using known molecular techniques. The advantages of the transformation method are that isolated enzyme genes, genes from diverse biological sources and/or anti-sense constructs (not just sense constructs) may be incorporated in the recipient plant genome.

Preferably the recipient plant is of the family Gramineae and most preferably of the species *Zea mays*. Other recipient plants may include rice, wheat, or barley, and fruit crops such as tomato.

The invention also provides a plant having one or more than one donor gene specifying an enzyme involved in a starch or glycogen biosynthetic pathway stably incorporated into its genome such that its ability to produce starch is altered. Such plants may have an improved capacity to produce starch at elevated or lowered temperature, and/or an ability to synthesise starch with an altered fine structure. Hence such plants are capable of producing higher starch yields at certain temperatures and/or are capable of producing starch with an improved quality.

The variety of possible plants, donor genes and resulting effects have been discussed previously.

The invention also provides the seeds and progeny of such plants, and hybrids whose pedigree includes such plants.

The present invention will now be described, by way of illustration, by the following description and examples with reference to the accompanying drawings of which:

FIG. 18 shows the nucleotide sequence for *E coli* glycogen synthase.

EXPERIMENTAL BACKGROUND TO THE INVENTION

Figure 1:
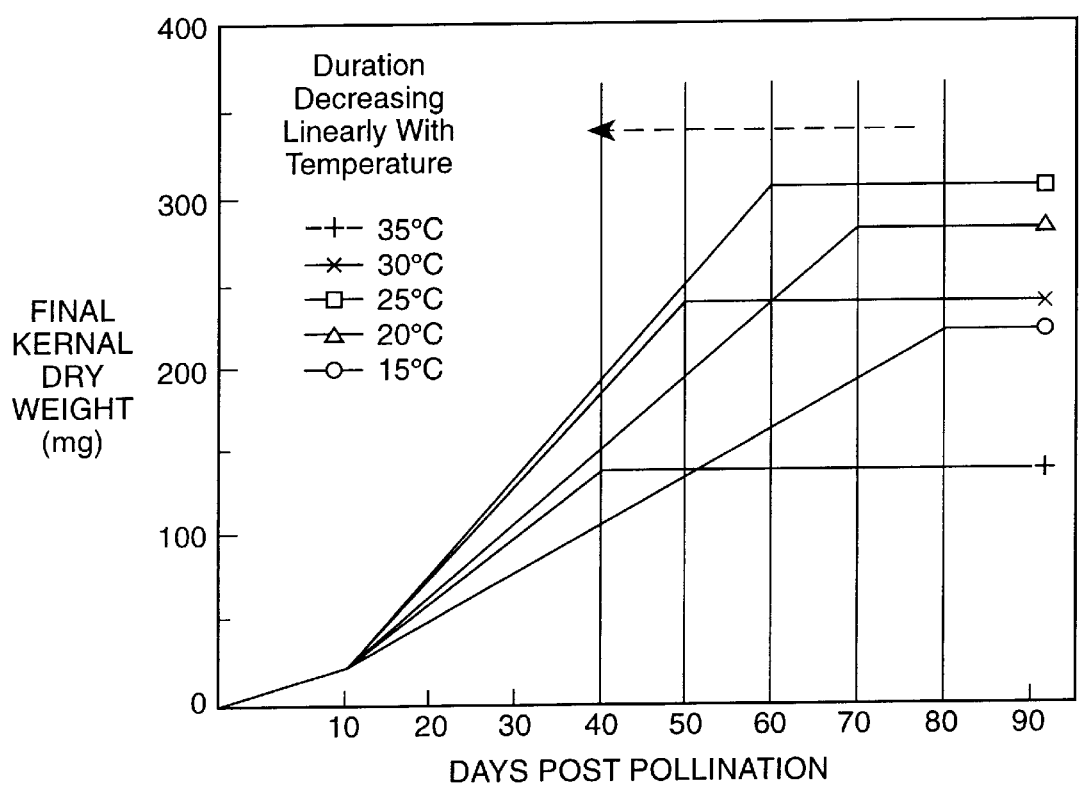
FIG. 1 is a graph showing the effect of temperature on final grain weight.
Figure 2:
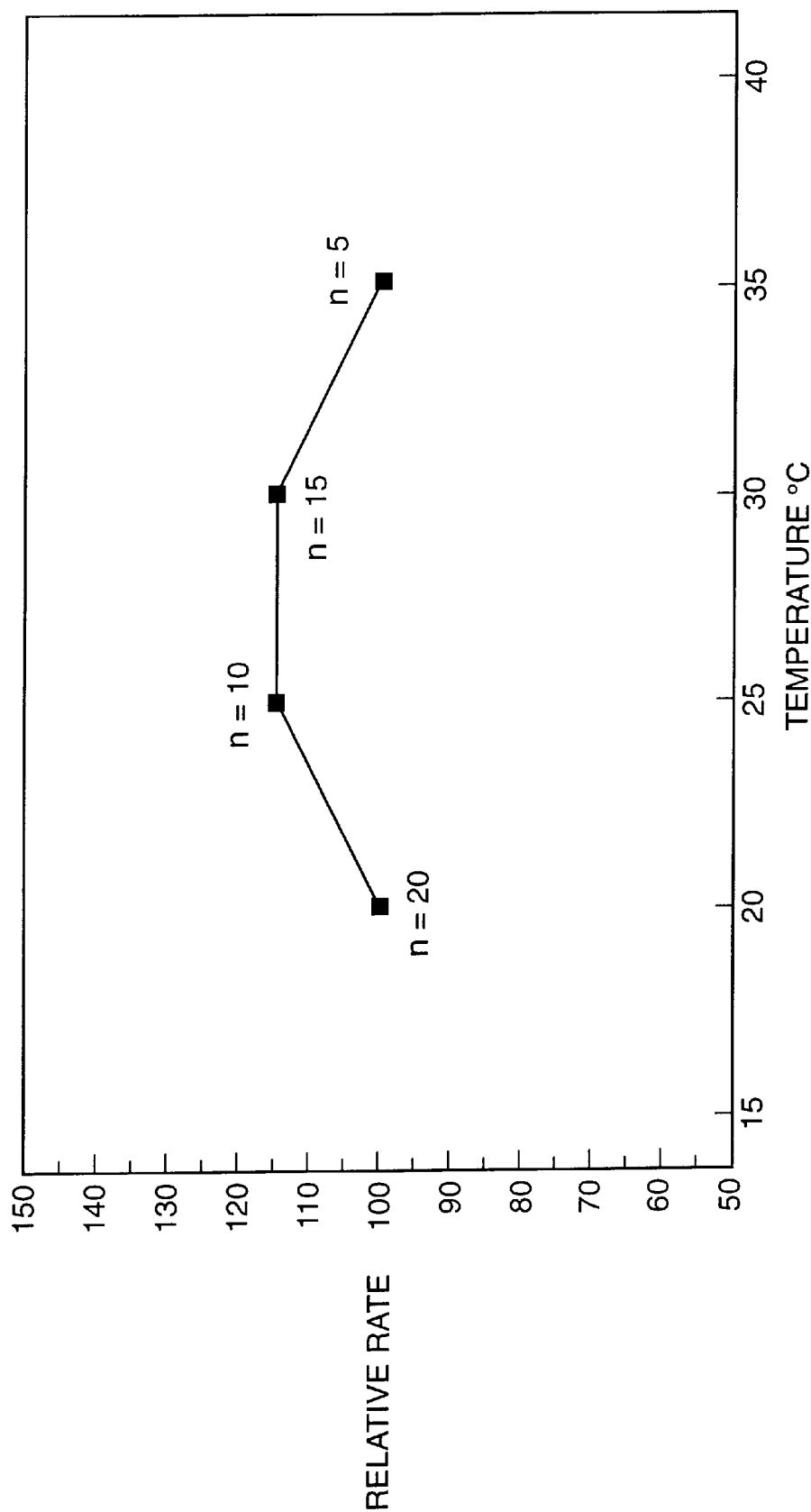
FIG. 2 is a graph of starch synthesis rate against temperature.

In order to examine in detail the relationship between starch synthesis rate and temperature in vivo, we have conducted experiments on maize plants growing under defined temperature regimes in constant environment cabinets. In these experiments the maize ears have been maintained at defined temperatures independently of the rest of the plant by means of thermostatically controlled glass fibre heating mantles placed around the ears. Rates of starch synthesis at precisely regulated temperatures were calculated from dry weight accumulation curves for the maize kernels over a defined period. The analysis of maize endosperm starch synthesis at different temperatures showed that the rate increases with temperature between 15 and 25° C. Between 25 and 30° C. there was no significant increase in rate. The rate at 35° C. was significantly lower than the rate at 30° C. (FIG. 2).

Figure 3:
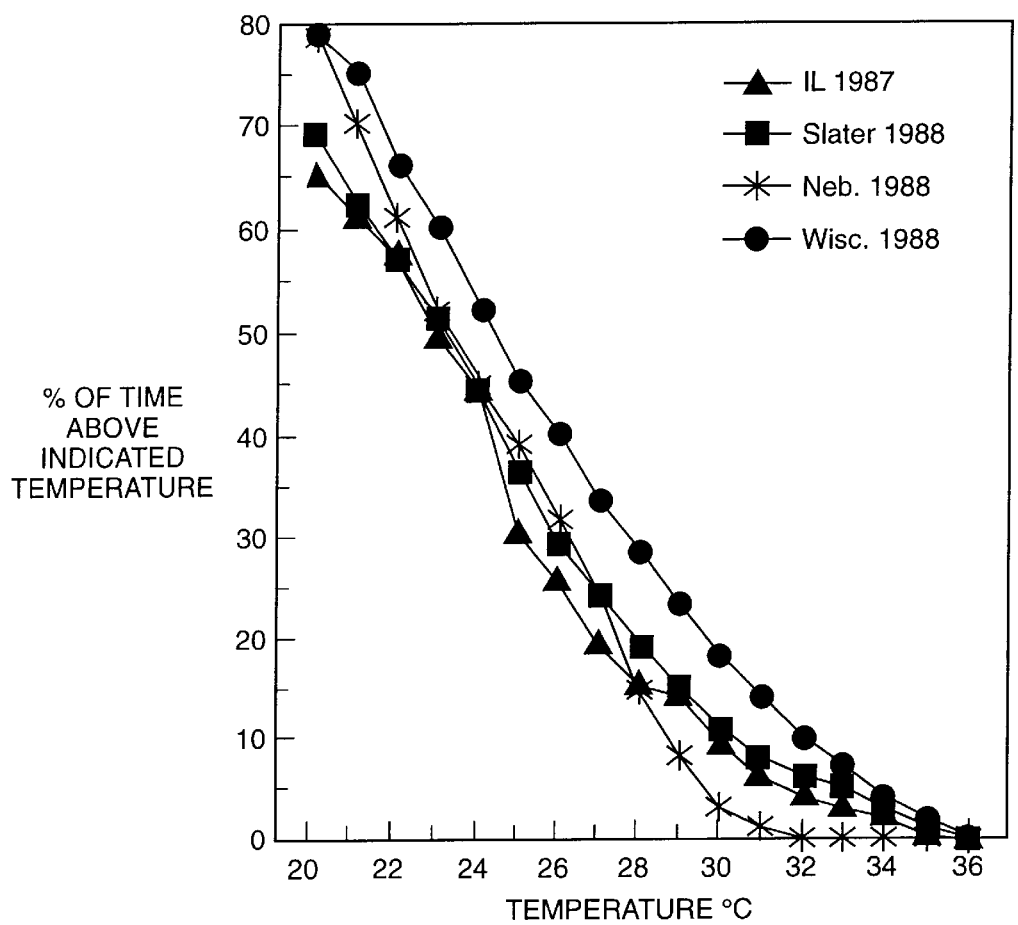
FIG. 3 is a graph of field temperature against time spent above that temperature.
Figure 4:
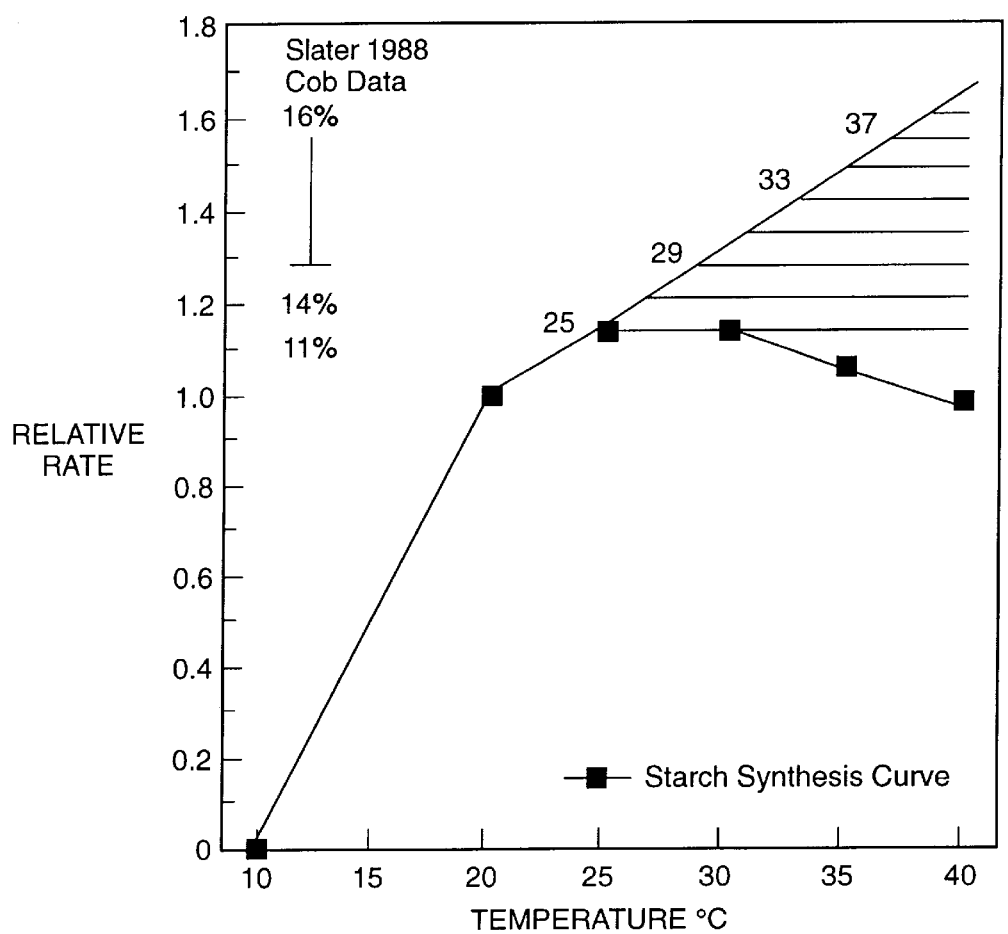
FIG. 4 shows computer simulations of different rate-models of temperature/activity profiles.

To examine the relevance of the in vivo starch accumulation rate versus temperature curve in the field, we monitored field temperatures during the starch filling period at various field stations in the mid-west of the United States. Air temperatures were monitored using a thermocouple attached to a recording device which recorded temperatures at five minute intervals. In addition, temperatures within the maize kernels were recorded by inserting thermocouples into the grain. Significant periods of time are spent above the optimal temperature (FIG. 3). We used computer modelling techniques to calculate the expected yield benefits of altering the in vivo starch synthesis versus temperature curves in several defined ways (FIG. 4). For example, increasing the temperature optimum for grain filling rate from 25 to 30° C. gives an anticipated yield benefit in excess of 10% over the years which we have recorded (Table 1).

TABLE 1

Computed increases in yield for a 5° C. increase in temperature optimum

| Location | Year | Real Rate Model | |
|---|---|---|---|
| | | Air | Cob |
| Cisco, Illinois | 1986 | 11.4% | — |
| Cisco, Illinois | 1987 | 15.9% | — |
| Slater (1) Iowa | 1988 | — | 15.7% ±1.2 |
| Slater (2) Iowa | 1988 | 15.9% | 15.9% ±0.2 |
| Cottage Grove Wisconsin | 1988 | 20.4% | 24.1% ±1.1 |
| Wood River Nebraska | 1988 | 15.8% | 15.7% ±0.7 |

In addition to in vivo information on temperature dependence, we have obtained in vitro evidence on the biochemical basis for the temperature dependence. We applied $^{14}$C-glucose to developing maize grain in vitro at different temperatures and measured the flux of radioactivity through different pathways. Using 1-$^{14}$C-glucose and 6-$^{14}$C-glucose it was possible to determine the in vitro rates of glycolysis and the pentose phosphate pathway as well as starch synthesis. The data in Table 2 below show that between 20 and 40° C. there was no significant increase in the rate of starch synthesis, though the flux of radioactivity through the pentose phosphate pathway and glycolysis increased approximately three-fold and two-fold respectively. The failure of the starch synthesis rate to increase above 25° C. is therefore due to the starch synthesis enzymes in the amyloplast (i.e. any one or any combination of soluble and bound starch synthase, branching enzyme and ADP-glucose pyrophosphorylase), and not due to a failure in the supply of sucrose or ATP at high temperatures.

TABLE 2

Effect of temperature on radioactivity released as carbon dioxide or incorporated into starch from 1-14C and 6-14C glucose

| | Temperature | |
|---|---|---|
| | 20° C. | 40° C. |
| Krebs Cycle mmol CO2/hr/endosperm | 14.8 ± 6 | 33.4 ± 8 |
| Pentose P. pathway mmol CO2/hr/endosperm | 3.8 ± 3 | 11.3 ± 3 |
| Starch mmol glucose/hr/endosperm | 45.7 ± 4 | 54.9 ± 7 |

To analyse further the biochemical basis for the temperature optimum for grain filling rate in cereals, we measured the activities with respect to temperature of most of the maize endosperm enzymes in the pathway for converting sucrose to starch, including soluble starch synthase (SSS) and branching enzyme (BE). Two aspects have been studied:

(1) The temperature dependence of the rates of the reactions catalysed by these enzymes; and, (2) The stabilities of the individual enzymes during incubations at different temperatures both in vivo and in vitro.

The glycogen synthase enzyme has also been studied (see (3) below).

(1) Temperature Dependence

Figure 5:
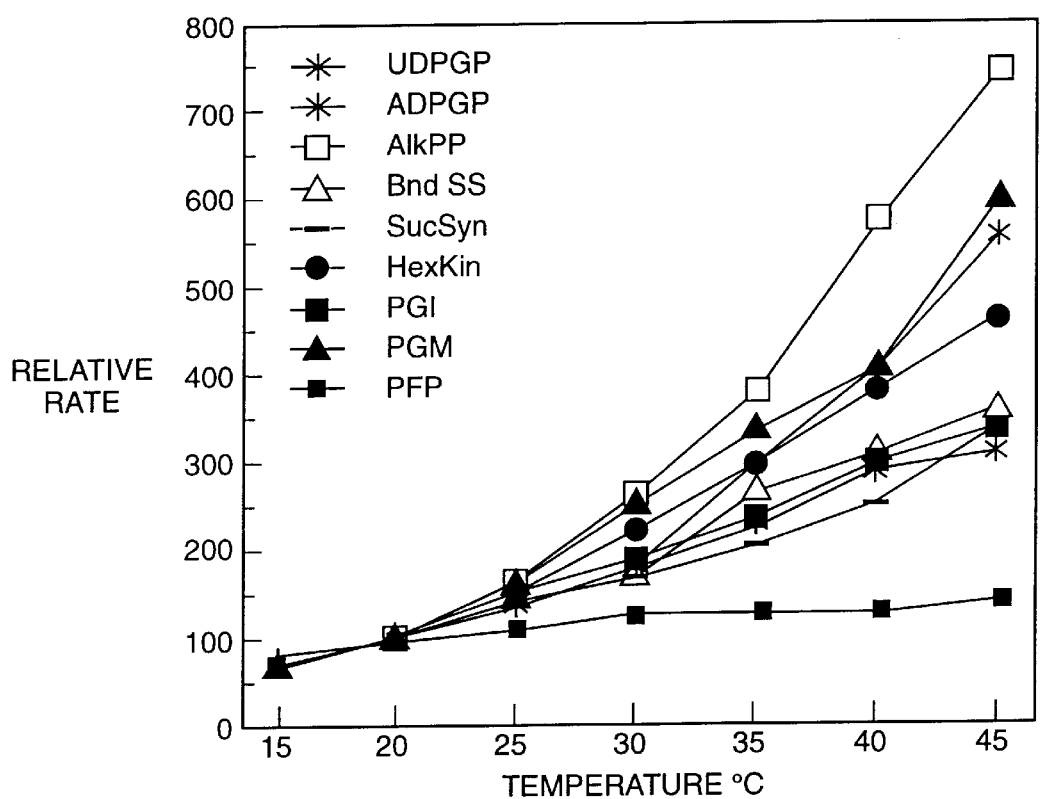
FIG. 5 is a graph of rate against temperature for several starch-synthesising enzymes.
Figure 6:
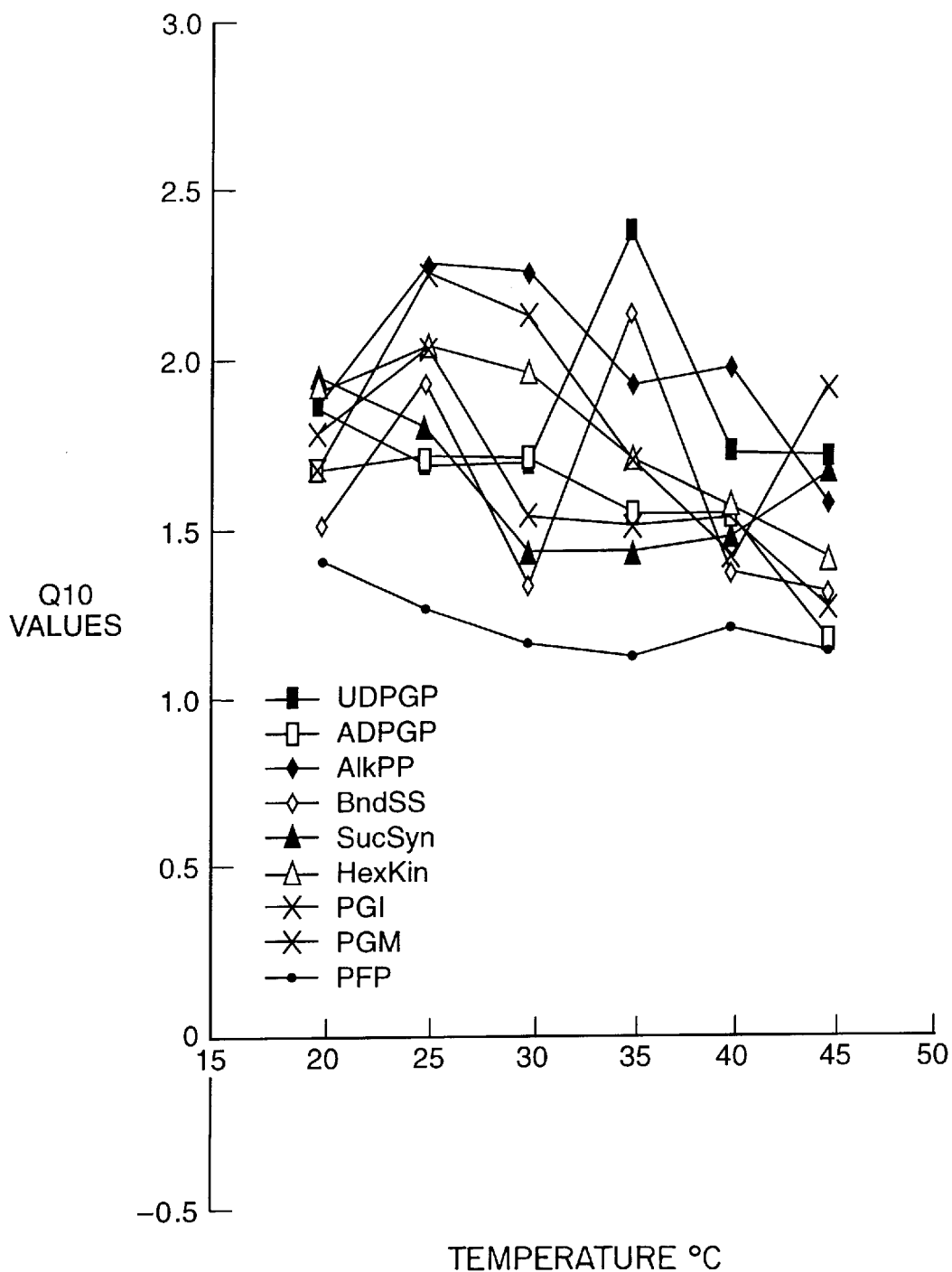
FIG. 6 is a graph of $Q_{10}$ values against temperature for several starch-synthesising enzymes.

The reaction rates of most of the enzymes studied (alkaline pyrophosphatase, phosphoglucomutase, UDP glucose pyrophosphorylase, hexokinase, phosphoglucosisomerase, sucrose synthase, ADP glucose pyrophosphorylase and bound starch synthase) have activities which increase with temperature at least up to 45° C. (FIG. 5). This temperature exceeds the highest temperature recorded during grain filling in the field. When replotted as $Q_{10}$ values (FIG. 6) it is clear that these enzymic reactions are stable across this temperature range. This is consistent with the theoretical expectation from the Arrhenius equation referred to above.

Figure 7:
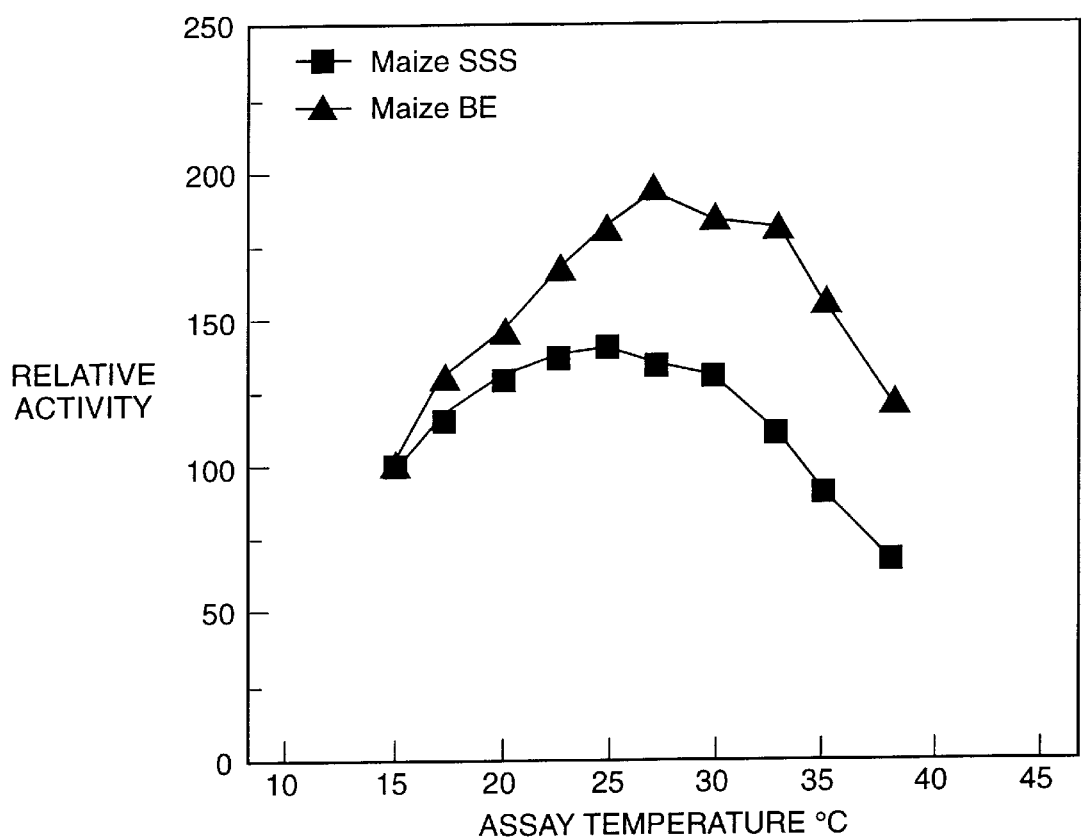
FIG. 7 is a graph of rate against temperature for maize endosperm soluble starch synthase and branching enzyme.

The temperature responses of SSS and BE were, however, a complete contrast (FIG. 7). The apparent temperature optima for activity are 25° C. for SSS and 27.5° C. for BE. When replotted as $Q_{10}$ values (FIG. 8) it is clear that there is an apparently constant decline in enzymic efficiency with increasing temperature. This is indicative of some decrease in catalytic activation brought about by depressed interaction between the enzyme and its substrates. As these are the only enzymes in the pathway with temperature optima for activity below 30° C., it is apparent that one or both of SSS and BE are "rate limiting" for starch synthesis between 20 and 30° C. The failure of starch synthesis rate in vivo to increase with temperature between 25 and 35° C. must be due to a failure of the activities of one or both of these enzymes to increase in activity over this temperature range.

Figure 8:
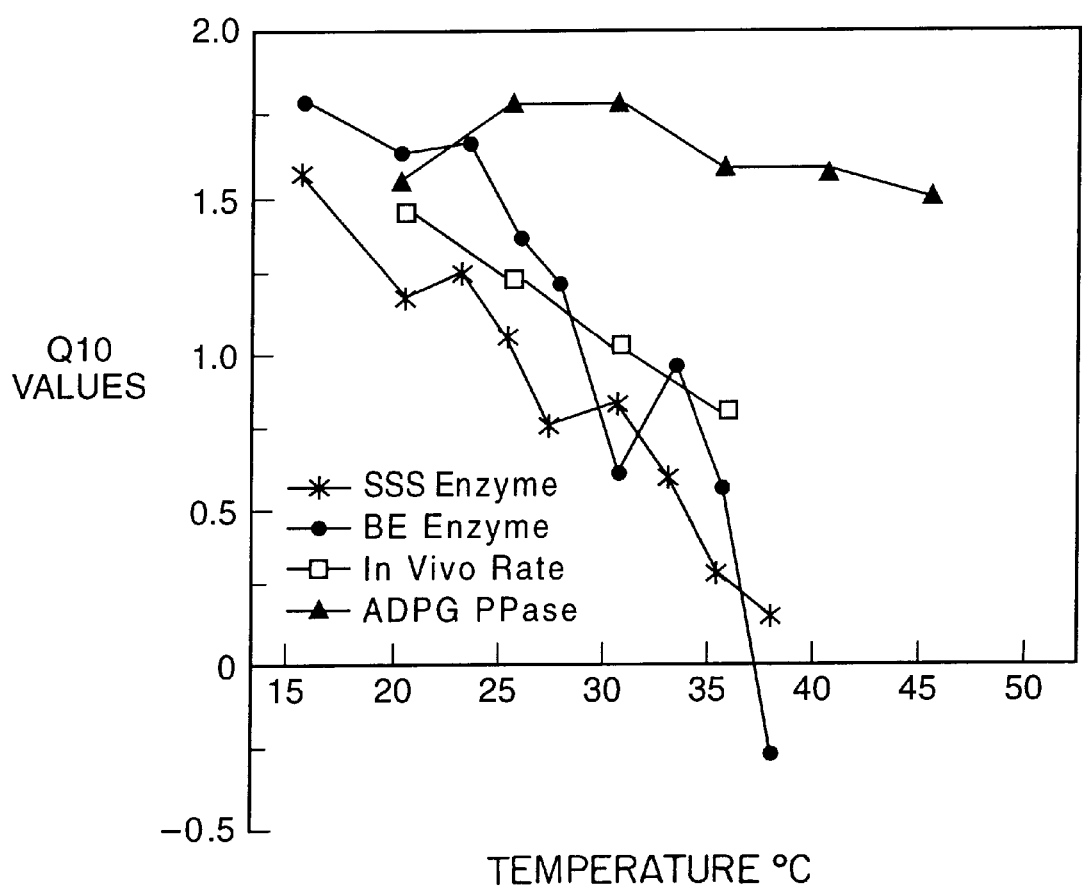
FIG. 8 is a graph of $Q_{10}$ values against temperature for maize endosperm soluble starch synthase and branching enzyme.

Grain has been sampled from maize plants grown at 20, 25 and 30° C. and SSS and BE activity has been measured over several temperatures. The temperature at which the grain are growing was found to have no effect on the temperature optima for activity of these two enzymes. Temperature activity curves for these two enzymes from the endosperms of several commercial U.S. maize hybrids show the same temperature optima. As shown in FIG. 8, $Q_{10}$ values for in vivo rates and SSS and BE activities show remarkable similarities. This is in contrast to, for example, ADP-glucose pyrophosphorylase where $Q_{10}$ is fixed across different temperatures as predicted by the Arrhenius equation.

Figure 9:
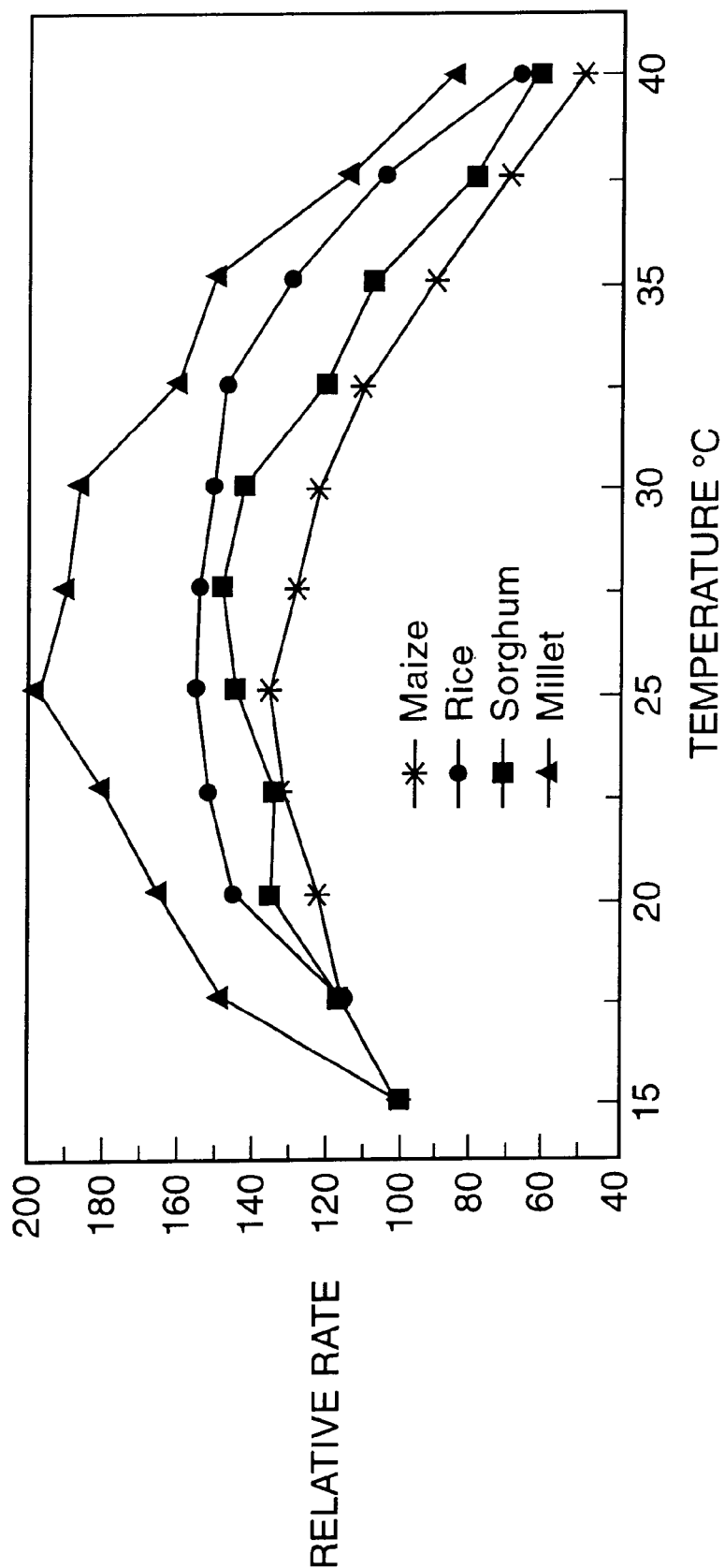
FIG. 9 is a graph of rate against temperature for rice, maize, sorghum and millet soluble starch synthase.
Figure 10:
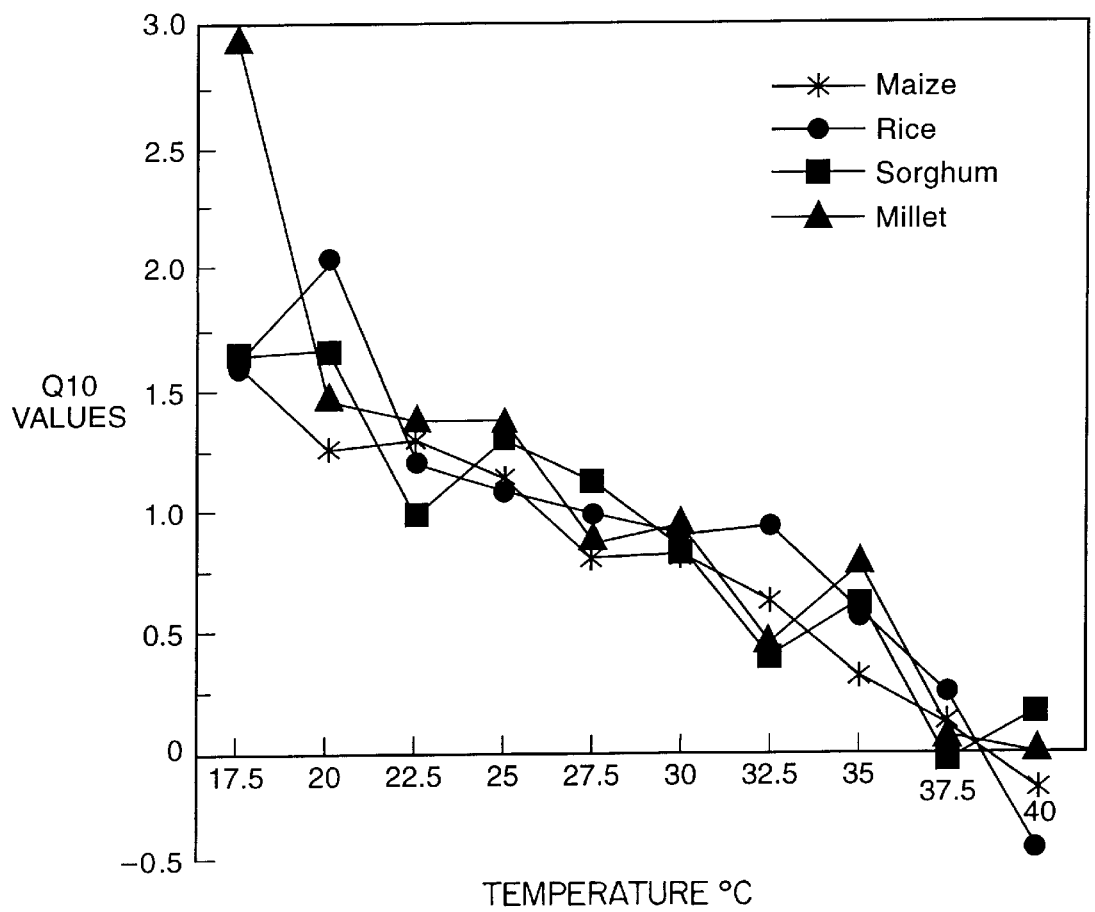
FIG. 10 is a graph of $Q_{10}$ values against temperature for rice, maize, sorghum and millet soluble starch synthase.

Comparisons of the temperature activity curves for SSS from maize, rice, sorghum and millet show that the temperature optima for activity were consistently around 25° C. (FIG. 9). There were, however, differences in $Q_{10}$ between 15 and 25° C., the $Q_{10}$ increasing in the order maize, sorghum, rice and millet (FIG. 10), that is, in the order of increasing climatic temperatures of the locations where the crops are grown. Further studies of dicot plants has led to the discovery that the $Q_{10}$ for SSS can be considerably higher in some plants than we have observed in the monocot plants so far studied. For example in tomato leaf and fruit the $Q_{10}$ values were significantly higher than that seen in maize (FIG. 9).

High increases in $Q_{10}$ between 15 and 25° C. mean that SSS may not become rate limiting at 25° C., pathway rate control being passed to another enzyme(s). The in vivo rate of flux through the starch pathway may, therefore, continue to increase with temperature above 25° C.

The temperature activity curves of the green leaf tissue forms of SSS and BE are similar to those observed for the developing grain. These enzymes, we conclude, limit photosynthesis at temperatures above 25° C.

The temperature activity curves of the developing tassel forms of SSS and BE are similar to those observed for the developing grain forms, again confirming that these two enzymes limit starch synthesis at temperatures above about 25° C.

(2) Temperature Stability

Experiments with both wheat and maize have confirmed that increased temperature not only affects the rate of enzyme catalysed reaction of SSS, but also results in enzyme instability resulting in long term loss of enzyme activity. We have termed this phenomenon "knockdown" in order to distinguish it from the changes in reaction rate described above. "Knockdown" is defined as the change in maximum catalytic activity assayed at 20° C. following a heat treatment of the enzyme either in vitro or in vivo at a higher temperature.

Figure 11:
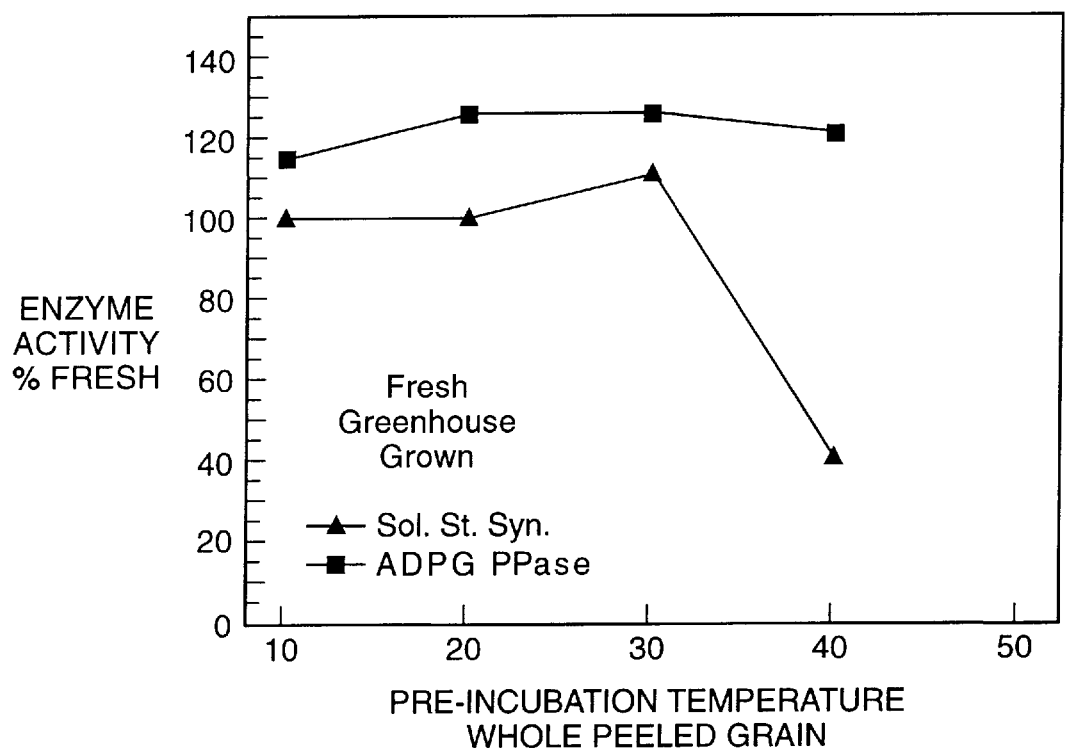
FIG. 11 is a graph showing soluble starch synthase and ADPG pyrophosphorylase activity against pre-incubation temperature.
Figure 12:
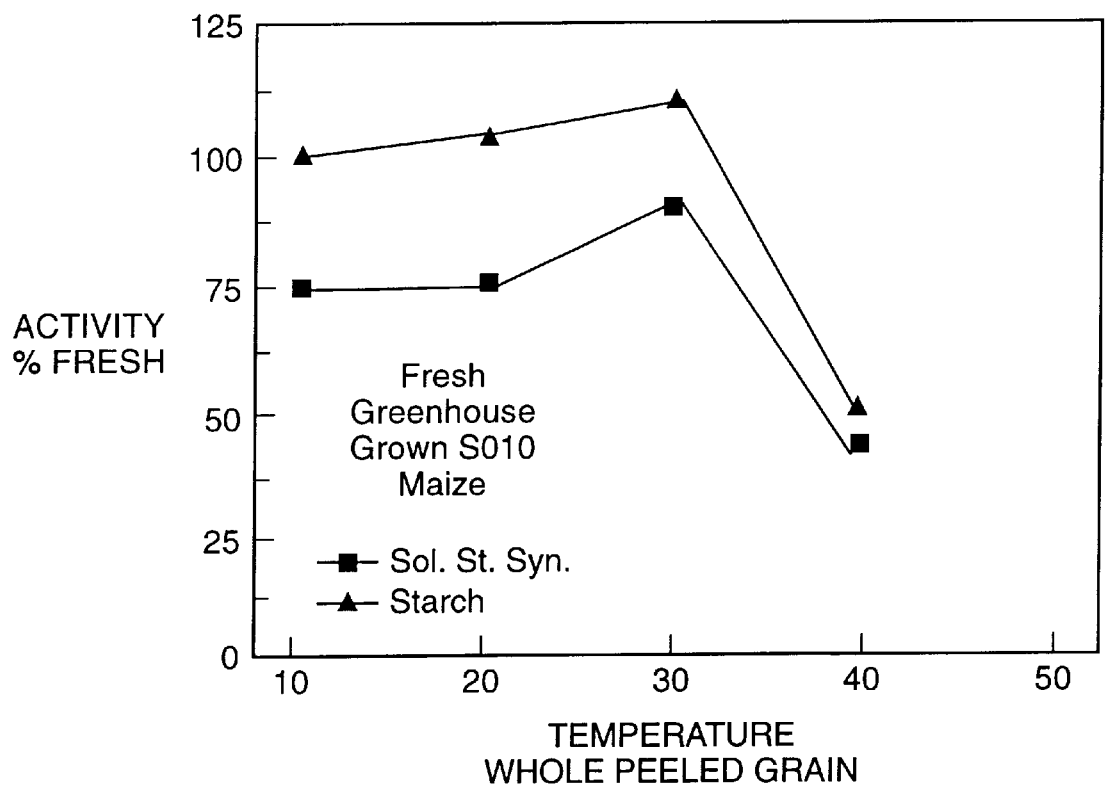
FIG. 12 is a graph showing soluble starch synthase activity and starch synthesis against pre-incubation temperature.

Incubation of extracted maize endosperm SSS in vitro at temperatures up to 37° C. did not cause any loss of enzyme activity when subsequently assayed at 20° C. At temperatures higher than 37° C., however, progressive long term loss of enzyme activity occurred, such that by 40° C., 80% of the enzyme had become inactivated. When peeled maize grains were preincubated for three hours at 40° C., there was a significant drop in SSS activity when subsequently extracted and assayed at 20° C. (FIG. 11). In contrast the extractable activity of ADP-glucose pyrophosphorylase was not altered by this same preincubation. Pre-treatments for three hours at 10, 20 or 30° C. did not result in any drop in the activity of SSS. Similar in vitro incubations of wheat grain resulted in substantial loss of SSS activity at temperatures as low as 30° C. while ADP-glucose pyrophosphorylase activity was unaffected. The drop in SSS activity at 40° C. coincided with a drop in starch synthesis measured as $^{14}C$ incorporation into starch assayed in-vitro (FIG. 12).

Figure 13:
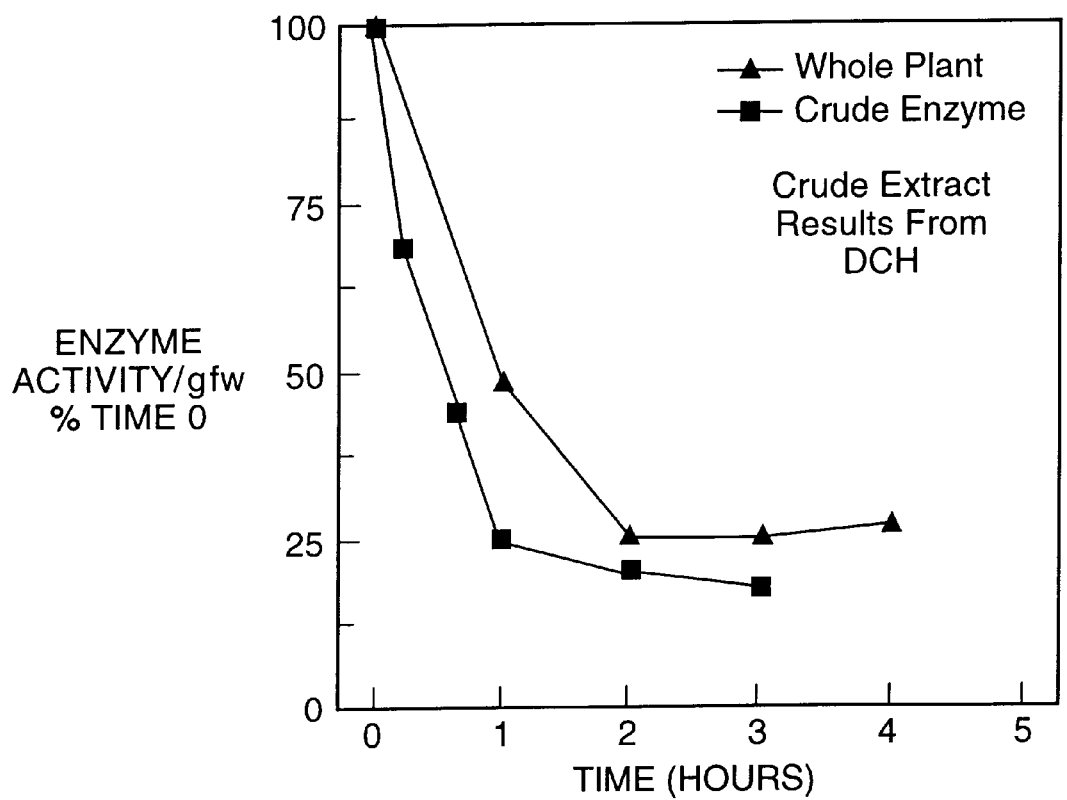
FIG. 13 is a graph showing soluble starch synthase activity against time after pre-incubation at 40° C.
Figure 14:
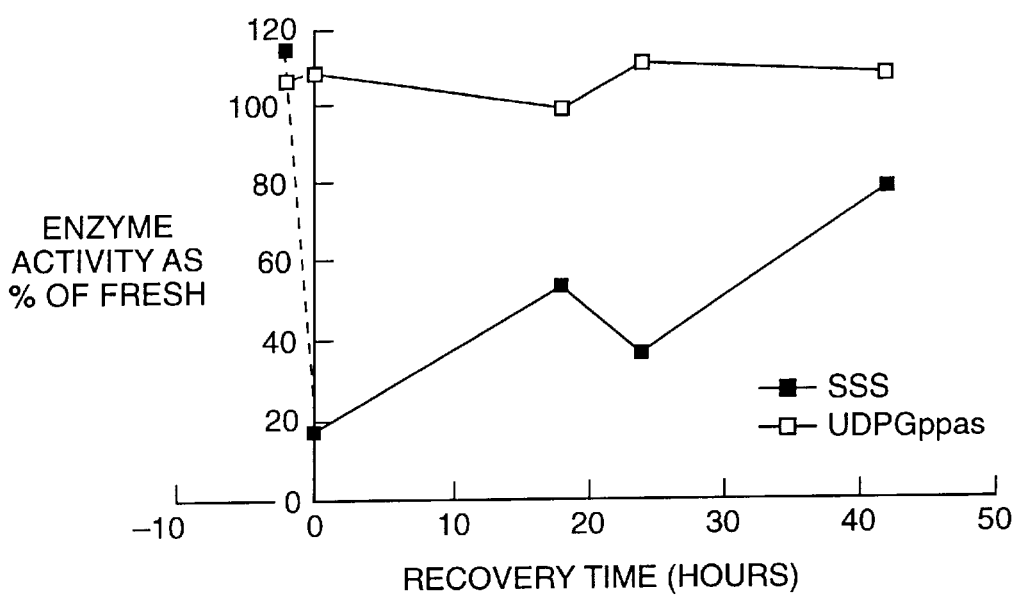
FIG. 14 is a graph showing recovery of soluble starch synthase and UDPG pyrophosphorylase activity against time after heat treatment.

In experiments in which maize ears were heated in situ on the plant, temperatures in excess of 37° C. caused loss of SSS activity when subsequently extracted and assayed at 20° C. The activity of ADP-glucose pyrophosphorylase was, again, unaffected by this treatment. Following heat treatments at 40° C. for a range of times, it was found that the extractable SSS activity declined dramatically over a two hour period (FIG. 13). When the cobs were returned to 20° C. following a period at 40° C., the extractable SSS activity only returned to its initial activity after a period of 24 hours at the lower temperature (FIG. 14). Similar experiments with wheat ears also showed that knockdown of SSS occurred in vivo at temperatures of 30° C. and above. Recovery of SSS activity in wheat also took over 24 hours.

(3) Temperature Dependence of Glycogen Synthase

The biochemical reaction catalysed by soluble starch synthase (ADPGlucose:1,4-α-D-glucan4-α-D-glucosyltransferase (E.C. 2.4.1.21)) involves the sequential addition of glucose donated from the sugar nucleotide ADPGlucose to a glucan chain using an α-1,4 linkage. Other sources of this chemical reaction exist in nature as the enzymes glycogen synthase notable from bacteria (ADPGlucose: 1,4-α-D-glucan4-α-D-glucosyltransferase (EC2.4.1.21)) and animals (UDPGlucose:glycogen 4-α-D-glucosyltransferase (EC2.4.1.11)).

Figure 15:
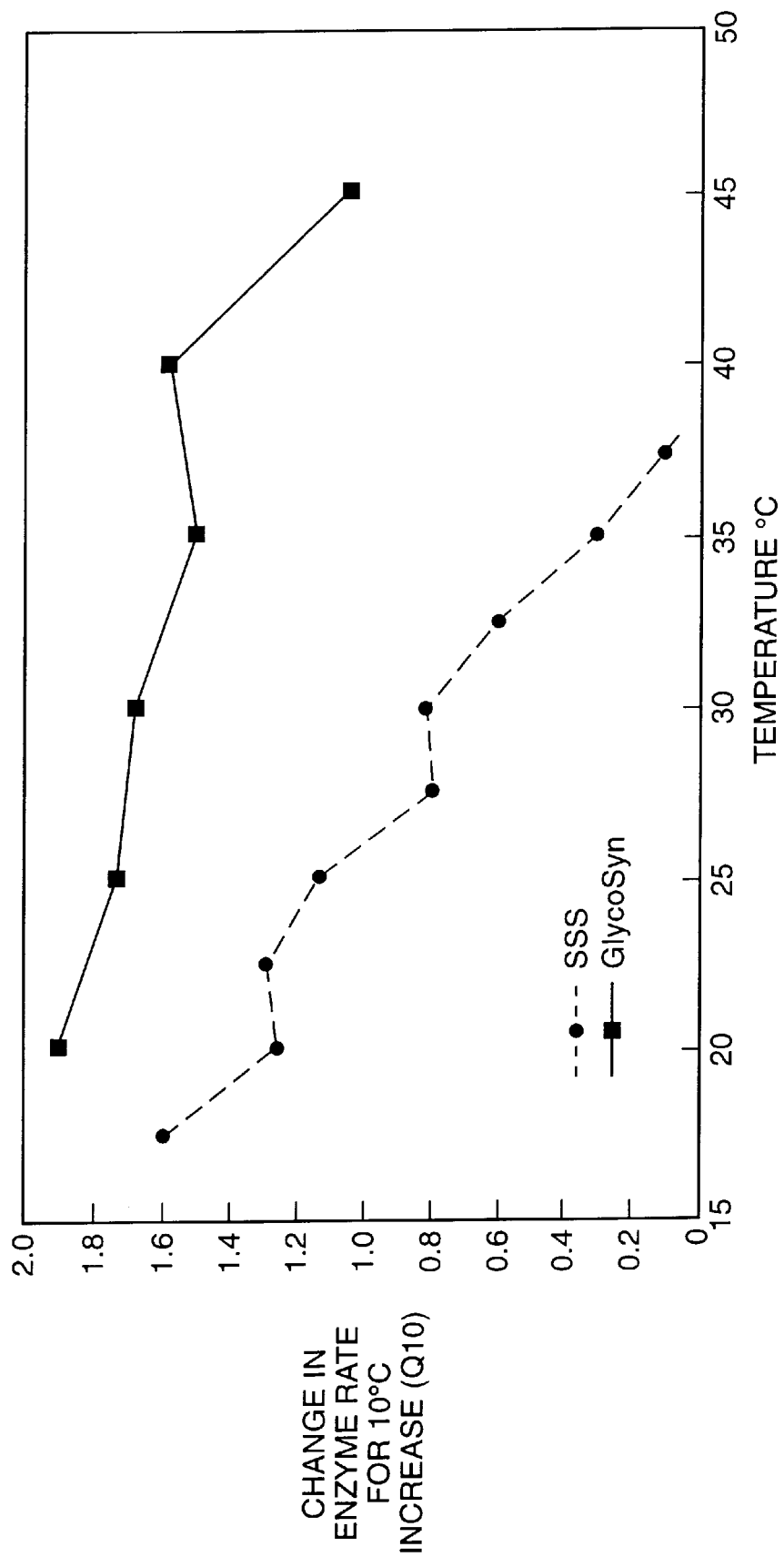
FIG. 15 is a graph showing $Q_{10}$ values of soluble starch synthase and glycogen synthase against temperature.

When we studied the temperature dependence of the glycogen synthase reaction we found that there was a remarkable increase in activity with increasing temperature. This was in dramatic contrast to the temperature dependence of the reaction catalysed by soluble starch synthase (FIG. 15). The biochemical cause of this new temperature response of glycogen synthase indicates that this enzyme can maintain its normal activation energy for the reaction even at higher temperatures that reduce SSS activity. The glycogen synthase enzymes catalytic site is either able to tolerate the higher temperature or else is able to compensate for possible changes in the conformation of the substrate itself. Thus because glycogen synthase catalyses the same chemical reaction as SSS, it has very wide application as a means of increasing plant starch deposition at higher temperatures.

The nucleotide and amino-acid sequences of glycogen synthase are known (i) from E.Coli GenBank/EMBL #J02616 (Kumar et al, J Biol Chem 34 16256–16259 (1986)), (ii) from rabbit skeletal muscle (Hang et al, FASEB J 3 3532–3536 (1989)), and (iii) from human muscle (Browner et al, Proc Nat Acad Sci 86 1443–1447 (1989)). The bacterial (ADPGlucose: 1,4-α-D-glucan-4-α-D-glucosyltransferase (EC 2.4.1.21)) and animal (UDPGlucose: glycogen 4-α-D-glucosyltrasferase (EC 2.4.1.11)) sequences are NOT homologous. Furthermore the bacterial forms are not phosphorylated and also are not allosterically affected by glucose 6-phosphate. Finally, the bacterial enzyme uses ADPG (ie, like plants) and only the animal forms use UDPG. This makes the bacterial enzyme the ideal choice for using on plants. The structural genes for the bacterial glycogen synthase are mapped to pOP12 in E.Coli and glycogen synthase map to glgA. Nucleotide sequencing further refines the position of glgA. The translation start of glgA is known to be immediately after glgc and the nucleotide sequence determined. The $NH_2$ sequence was known so that the actual start of the glgA gene was unambiguously determined as well as confirming the direction of transcription. The deduced amino acid sequence show complete homology with the known $NH_2$ sequence and with the known amino acid sequence. Different bacterial enzymes show 90% sequence homology. There is complete agreement between the reported and deduced amino acid sequences for the enzyme. Cells transformed with the gene produce a polypeptide that has sequence homology with the known amino acid sequences.

THE BIOCHEMICAL CAUSE OF THE TEMPERATURE EFFECT

Figure 16:
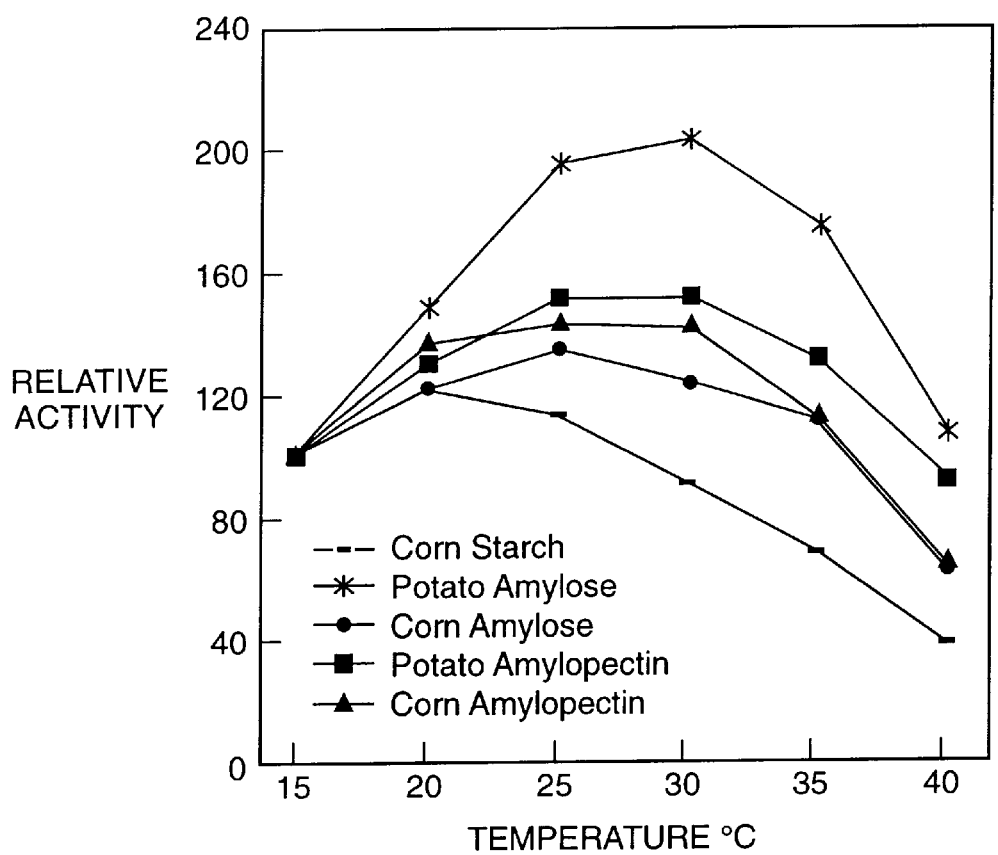
FIG. 16 is a graph of soluble starch synthase activity against temperature using various primers.
Figure 17:
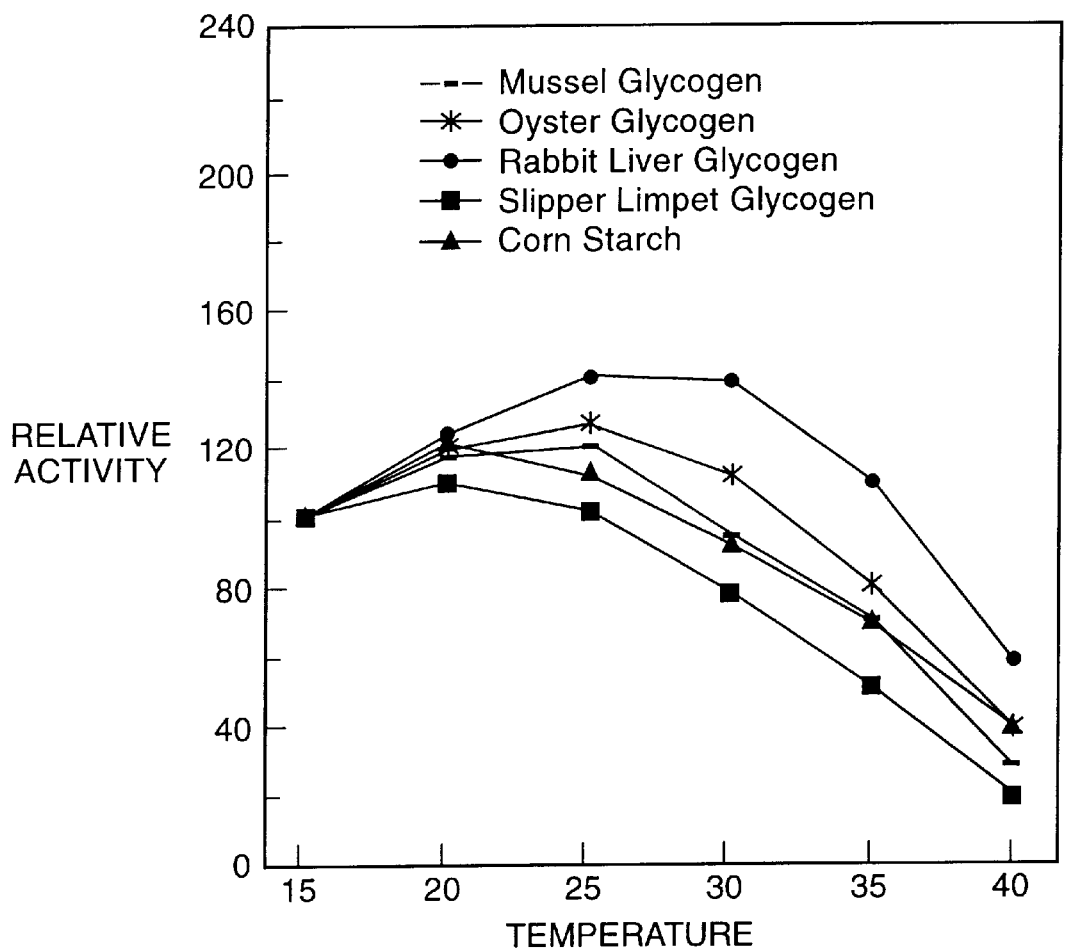
FIG. 17 is a graph of soluble starch synthase activity against temperature using various primers.

As was stated above, the $Q_{10}$ characteristics of an enzyme catalysed reaction is determined by the energy of activation of that enzyme. The atypical behaviour of SSS and BE to increasing temperature shows that the normal activation energy of this reaction which appears to be optimal at lower temperatures (for example, around 10° C.) is not carried through to the higher temperatures. The decay in enzyme rate with increasing temperature is indicative of some change in the interaction between the enzyme and its substrate. This could be due to a change in the enzyme catalytic site or else a change in the conformation of the substrate itself. Studies of the effects of different primers on the temperature-dependence of SSS activity shows that the precise temperature optimum is influenced by the nature of the substrate (FIGS. 16 and 17). Furthermore, when very low molecular weight primers were used in the enzyme reaction the temperature response curve was dramatically altered such that the $Q_{10}$ was 1.6 between 25 and 35° C. for maltotriose, maltotetrose and maltoheptose primers. Collectively these data indicate that the biochemical cause of the temperature optimum of SSS activity is related in some way to the molecular structure of starch and its interaction with SSS and BE.

STARCH FINE STRUCTURE ALTERATIONS

Figure 23:
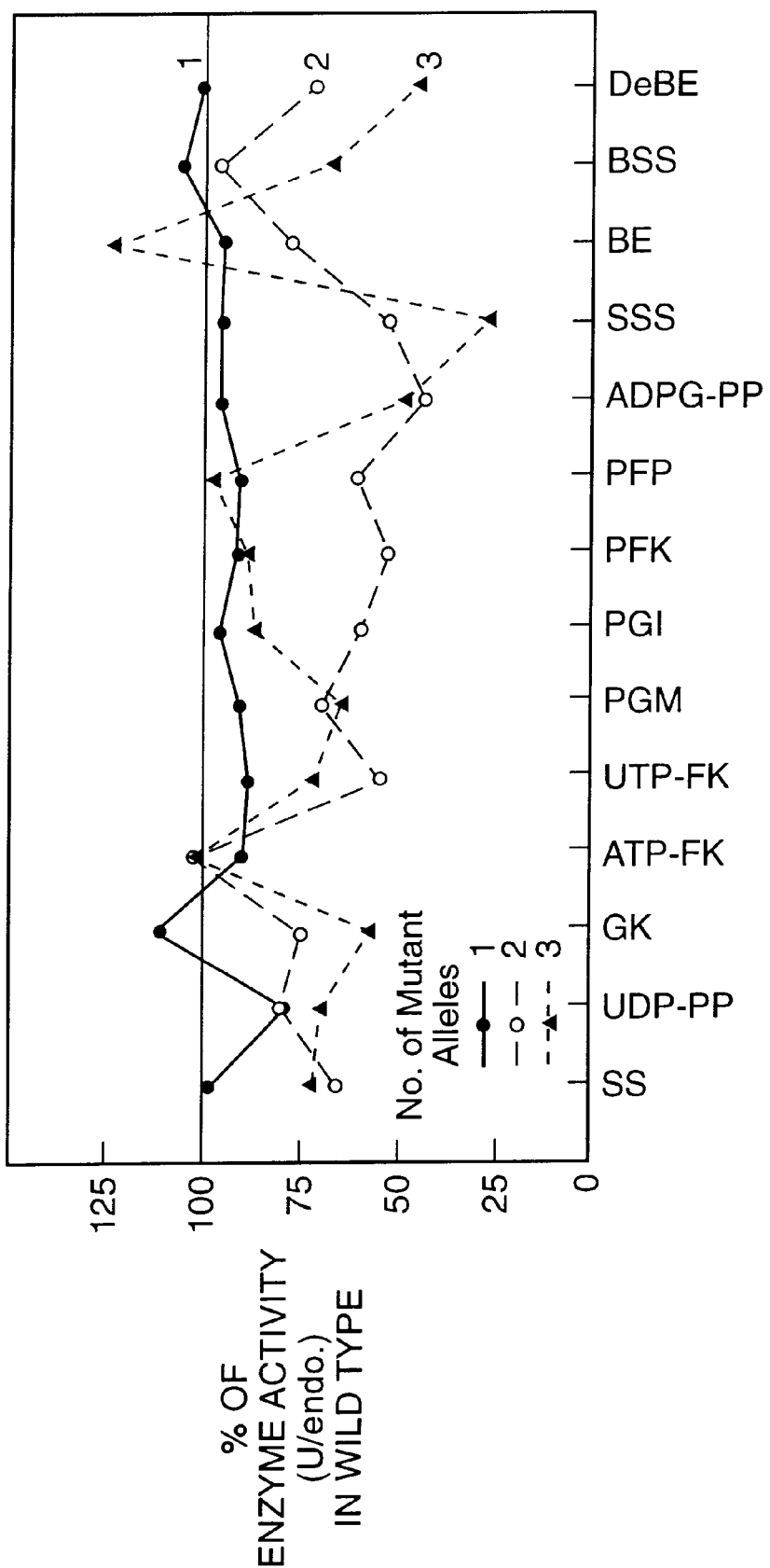
FIG. 23 shows activity of various starch synthesising enzymes at different gene doses in the sugary maize mutant.
Figure 24:
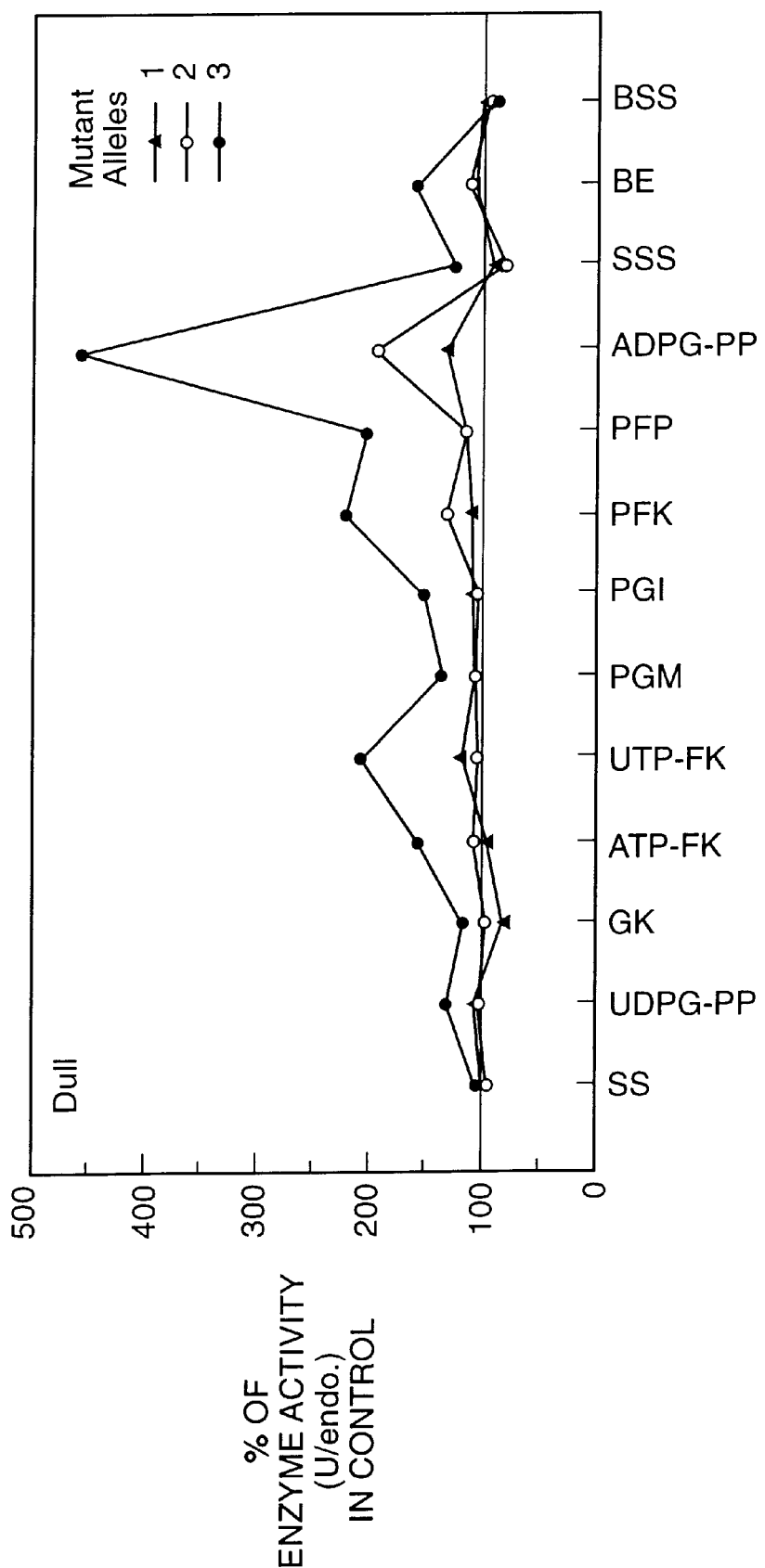
FIG. 24 shows activity of various starch synthesising enzymes at different gene doses in the dull maize mutant.
Figure 25:
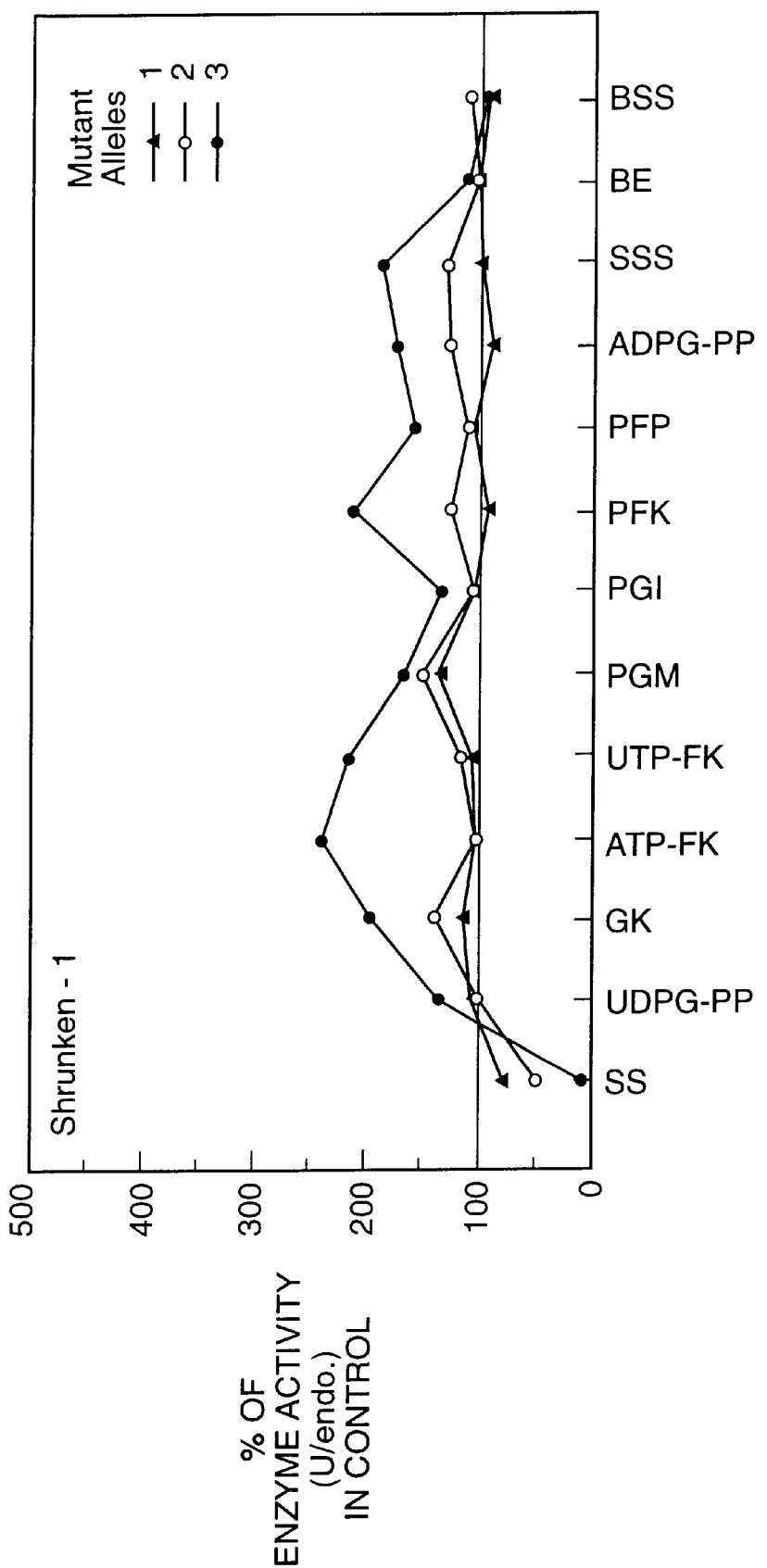
FIG. 25 shows activity of various starch synthesising enzymes at different gene doses in the shrunken maize mutant.
Figure 26:
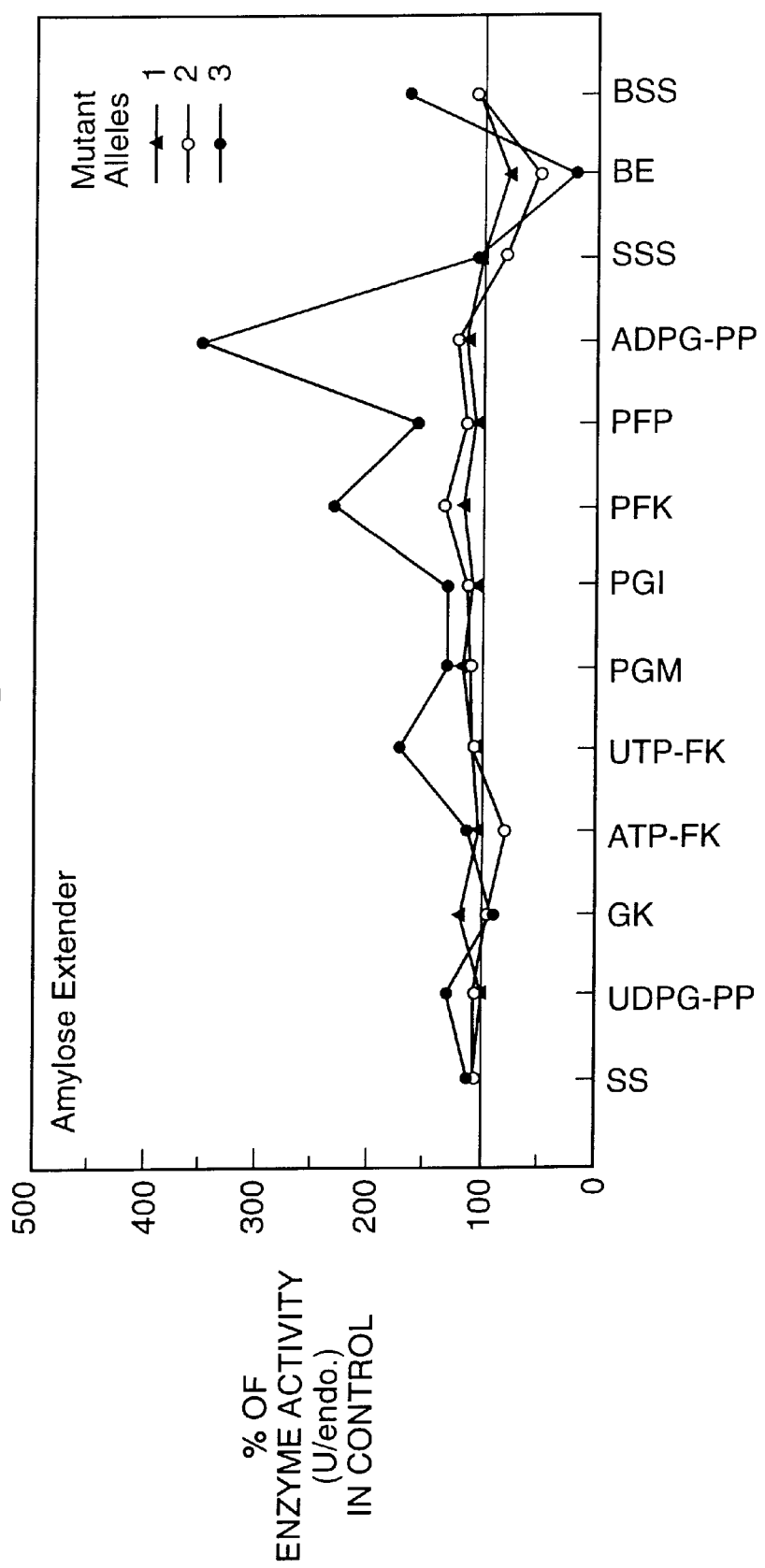
FIG. 26 shows activity of various starch synthesising enzymes at different gene doses in the amylose extender maize mutant.

Detailed studies of the starch mutants in corn (amylose extender, sugary, dull and waxy) has shown-us that the expression of enzyme activities is altered in these mutants such that there are new ratios of several enzymes involved in the pathway of starch synthesis. FIGS. 23 to 25 show the considerable over-expression of several enzymes in the pathway of starch synthesis, particularly where there is a specific lesion in the normal pattern of starch deposition. Furthermore we have found that not only is there a change in overall enzyme expression of some enzymes, but also there is an over-expression of some isoforms of SSS and BE enzymes. These mutations therefore not only cause a reduction in expression of SSS and BE enzymes, as has been reported in the literature, but there is apparently an over-expression of the other isoforms of these same enzymes in the pathway. This change in enzyme isoform expression occurs in response to or as a consequence of a change in flux of sugars to starch. There is then a resulting change in starch fine structure which has been documented in the literature, which is now known to be due to a combination of a reduction in expression of SSS and BE, together with an over-expression of other isoforms of SSS and BE which have different roles in the starch assembly process. These new findings from our ongoing work has led to our efforts to alter gene-expression levels of SSS and BE in cereal endosperm in order to effect a new starch structure in corn. Furthermore, since we now know that different isoforms have different roles in starch assembly there is the opportunity of transforming corn with forms of SSS and BE that have other different properties which will effect a change in the fine structure of the starch (eg using SSS and BE from other diverse biological sources of plants, animals, bacteria and fungi).

CONCLUSIONS FROM THE EXPERIMENTS

Our results have demonstrated that the failure of the starch synthesis rate in cereal endosperm to increase with temperature above 20–25° C. is due to the fact that in the temperature range of 25–30° C. the rate of starch synthesis is controlled by the activities of the SSS and BE enzymes. The rates of the reaction catalysed by SSS and BE fail to increase with temperature above 25° C. In addition, knock-down of SSS activity may further reduce yields in maize above 37° C. and in wheat above 30° C. Crops such as wheat, barley and maize frequently experience temperatures above 25° C. during their grain filling period. This invention increases the temperature optimum for the grain filling rate above 25° C. by relieving the limitations imposed by the reaction properties of SSS, BE or both. The enzyme glycogen synthase has a radically different response to temperature and is an ideal source of enzyme for increasing starch synthesis at temperatures that exceed the temperature optima of SSS and or BE. Changing the temperature optimum for starch synthesis in plants increases plant yield as well as changing other important properties such as fruit texture and sweetness.

Furthermore the alterations in expression levels of SSS and BE using both sense and antisense constructs results in an alterations in the fine-structure of the starch produced in the recipient plants. In addition, effecting this change in ratios of enzyme expression using temperature stable enzymes results in a more stable and defined type of starch quality that is unique to the recipient plants.

USE OF GLYCOGEN SYNTHASE

A gene encoding a glycogen synthase (GS) enzyme may be extracted from bacteria or animals and introduced into a donor plant by transformation.

The temperature sensitivity of starch synthesis may be improved by transforming plant genomes with a gene encoding glycogen synthase. Referring to FIG. 15 herewith, it can be seen that the activity of the glycogen synthase enzyme continues to increase with temperature at least to around 40° C., well in excess of the temperature maxima of the other plant enzymes, soluble starch synthase and branching enzyme, associated with starch synthesis. This data confirms the status of glycogen synthase as an enzyme with high Q10. It is also mentioned that the glycogen synthase temperature stability is better than any of the corn-derived enzymes from even the best of the germplasm which has been screened for this property.

Glycogen synthase catalyses the same reaction as soluble starch synthase [ADPglucose:1,4-α-D-glucan-4-α-D-glucosyltransferase (E.C. 2.4.1.21)] which catalyses the sequential addition of glucose donated from the sugar nucleotide ADP-glucose to a glucan chain using an α-1,4 linkage. Other sources of this α-1,4 linkage reaction exist in nature as the enzyme glycogen synthase, notably from bacteria [ADPglucose: 1,4-a-D-glucan 4-α-D-glucosyltransferase (E.C. 2.4.1.21] and animals [UDP-glucose: glycogen 4-α-D-glucosyltransferase (E.C. 2.4.1.11)]. Again the reaction involved is the sequential addition of glucose donated from a nucleotide sugar to a glucan chain via an α-1,4 linkage.

While not wishing to be bound by this particular explanation, it is believed that the different stability to increased temperature between soluble starch synthase and glycogen synthase is connected with changes in the structure of glucan chains at higher temperatures. It is generally agreed that the structure of starch (at least in solution) is a "statistical helix", that is, it exists as a dynamic mixture of structured helices and random coils. At temperatures much in excess of 20–25° C., the hydrogen bonding between the glucan double helices begins to break down, favouring the less organised random coil conformation. It is hypothesised that the active site of soluble starch synthase lies on the glucan chain when present as a helix whereas the glycogen synthase site of action is found on the random coil structure. By this reasoning, their enzymatic reaction may be the same but their temperature responses dramatically different.

The most favoured sources of the glycogen synthase gene for use in this invention are bacterial rather than animal sources for the following reasons:

(1) the bacterial glycogen synthase and plant soluble starch synthase both use ADPG, whereas the animal GS enzyme uses UDPG;

(2) the bacterial GS and plant SSS enzymes do not have any phosphorylation sites for activation, whereas the animal enzyme does; and, (3) the animal GS enzyme requires glucose-6-phosphate as a co-factor and is allosterically activated, whereas the plant SSS and bacterial GS enzymes are not.

For these reasons the bacterial GS gene is preferred. The nucleotide and amino acid sequences are known from the literature, for example, E.coli GenBank/EMBL #J02616 (Kumar et.al., J.Biol.Chem. 34, 16256–16259 (1986); rabbit skeletal muscle (zhang et.al., FASEB J. 3, 2532–2536 (1989); and, human muscle (Browner et.al., Proc, Natl.Acad.Sc. 86, 1443–1447 (1989).

The bacterial and animal GS sequences are not homologous. The structural genes for the bacterial GS are mapped to pOP12 in E.coli and glycogen synthase maps to glgA. Nucleotide sequencing further refined the position of glgA. The translation start point of glgA is known to be immediately following glgC and the nucleotide sequence determined. The $NH_2$ sequence was known so that the actual start of the glgA gene was unambiguously determined as well as confirming the direction of transcription. The deduced amino acid sequence shows complete homology with the known $NH_2$ sequence and with the known amino acid sequence. Different bacterial enzymes show 90% homology. There is complete agreement between the reported and deduced amino acid sequences for the enzyme. Cells transformed with the gene produce a polypeptide that has sequence homology with the known amino acid sequences.

FIG. 18 shows the nucleotide sequence for E.coli glycogen synthase as retrieved from EMBL #J02616 (SEQ ID NO:1). It is not a large protein: the structural gene is 1431 base pairs in length, specifying a protein of 477 amino acids with an estimated molecular weight of 49,000. It is known that problems of codon usage can occur with bacterial genes inserted into plant genomes but this is generally not so great with E.coli genes as with those from other bacteria such as those from Bacillus. Glycogen synthase from E.coli has a codon usage profile much in common with maize genes but it is preferred to alter, by known procedures, the sequence at the translation start point to be more compatible with a plant consensus sequence:

glgA - - - G A T A A T G C A G (SEQ ID NO:2)
cons - - - A A C A A T G G C T (SEQ ID NO:3)

The GS gene construct requires the presence of an amyloplast transit peptide to ensure its correct localisation in the amyloplast. It is believed that chloroplast transit peptides have similar sequences but other potential sources are available such as that attached to ADPG pyrophosphorylase (Plant Mol. Biol. Reporter (1991) 9, 104–126). Other potential transit peptides are those of small subunit RUBISCO, acetolactate synthase, glyceraldehyde-3P-dehydrogenase and nitrite reductase. For example,
Consensus sequence of the transit peptide of small subunit RUBISCO from many genotypes has the sequence:

MASSMLSSAAV - - - ATRTNPAQAS MVAPFTGLK-SAAFPVSRK QNLDITSIA SNGGRVQC (SEQ ID NO:4).

and the corn small subunit RUBISCO has the sequence: (SEQ ID NO:5)
MAPTVMMASSAT-ATRTNPAQAS AVAPFQGLK-STASLPVARR SSRSLGNVA SNGGRIRC The transit peptide of leaf starch synthase from corn has the sequence:(SEQ ID NO:6)
MA ALATSQLVAT RAGLGVPDAS TFRRGAAQGL RGARASAAAD TLSMRTASARA APRHQQQARR GGRFPSLVVC The transit peptide of leaf glyceraldehyde-3P-dehydrogenase from corn has the sequence:(SEQ ID NO:7)
MAQILAPS TQWQMRITKT SPCATPITSK MWSS-LVMKQT KKVAHSAKFR VMAVNSENGT The putative transit peptide from ADPG pyrophosphorylase from wheat has the sequence:(SEQ ID NO:8)
RASPPSESRA PLRAPQRSAT RQHQARQGPR RMC It is possible however to express the glycogen synthase constitutively using one of the well-known constitutive promoters such as CaMV35S but there may be biochemical penalties in the plant resulting from increased starch deposition throughout the entire plant. Deposition in the endosperm is much preferred.

Possible promoters for use in the invention include the promoters of the starch synthase gene, ADPG pyrophosphorylase gene, and the sucrose synthase gene.

Figure 19:
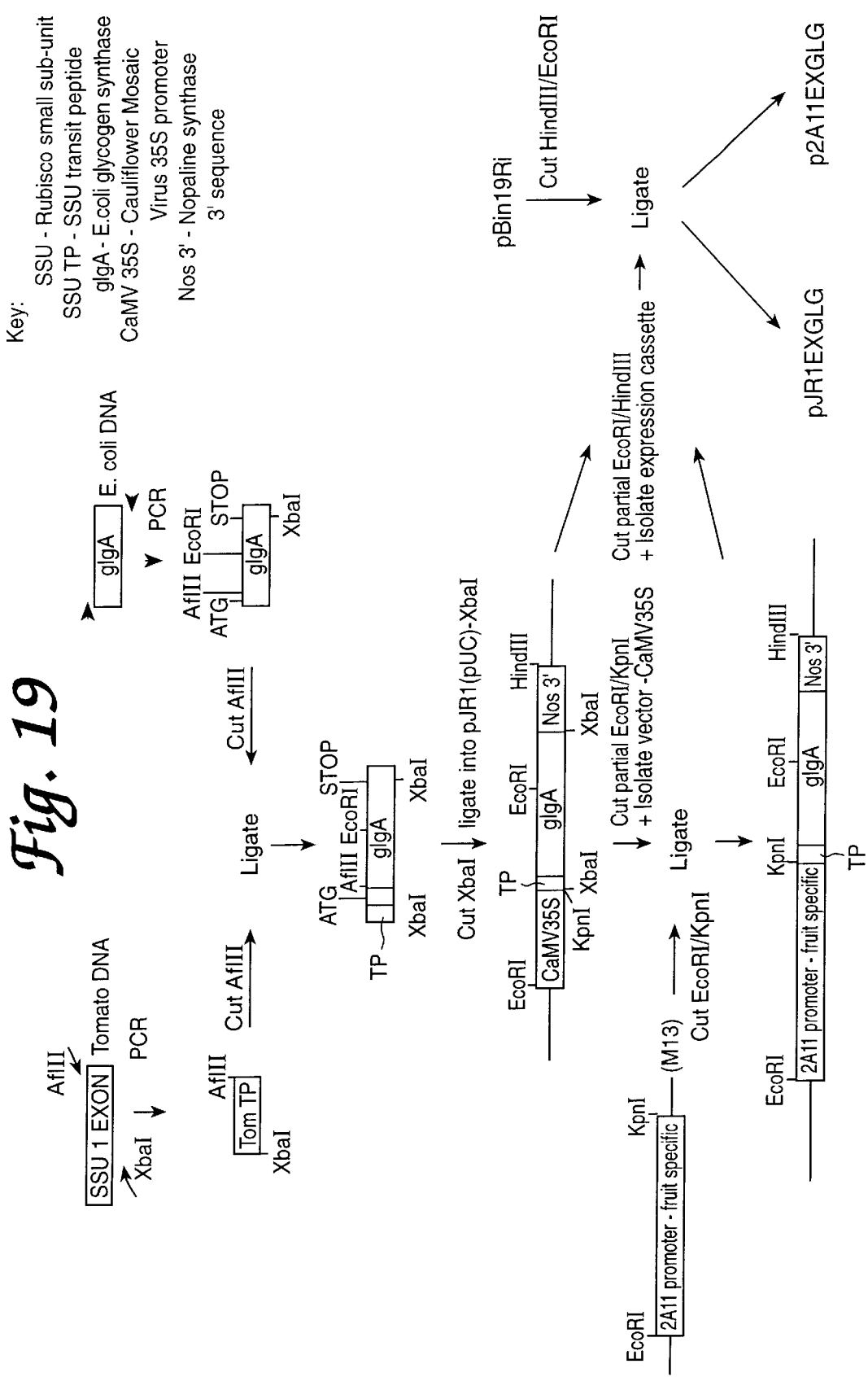
FIG. 19 shows the construction of two glycogen synthase transformation vectors.

FIG. 19 herewith illustrates the construction of two glycogen synthase vectors for use in this invention to transform tomato. Vectors are described with either constitutive or fruit-specific promoters. The transit peptide from tomato ribulose-bis-phosphate carboxylase is incorporated to direct the product to the plastid.

USE OF BACTERIAL BRANCHING ENZYME

Another embodiment of this invention is to use a temperature stable form of branching enzyme which can be obtained from bacteria. Branching enzyme [1,4-α-D-glucan: 1,4-α-D-glucan 6-α-D-(1,4-α-D-glucano) transferase (E.C. 2.4.1.18] converts amylose to amylopectin, (a segment of a 1,4-α-D-glucan chain is transferred to a primary hydroxyl group in a similar glucan chain) sometimes called Q-enzyme. Like soluble starch synthase, this reaction also has temperature-dependent properties in plants, presumably because of the same molecular mechanisms of helix-to-chain transitions. It is reasonable to believe that the bacterial BE enzyme will behave similarly.

The most favoured sources of the branching enzyme gene for use in this invention are bacterial although plant enzymes can also be used (rice endosperm, Nakamura etal., Physiologia Plantarum 84, 329–335 (1992); pea embryo, Smith, Planta 175, 270–279 (1988); maize endosperm, Singh and Preiss, Plant Physiology 79, 34–40 (1985); Vos-Scherperkeuter etal., Plant Physiology 90, 75–84 (1989)). The nucleotide and amino acid sequences for bacteria are known from the literature (Kiel JAKW et al, 1991, Mol Gen Genet, 230(1–2):136–144).

The structural genes for the bacterial BE are mapped to pOP12 in E.coli and branching enzyme maps to glgB.

The BE gene construct may require the presence of an amyloplast transit peptide to ensure its correct localisation in the amyloplast, as discussed previously for the glycogen synthase gene construct.

It is possible to express the branching enzyme constitutively using one of the well-known constitutive promoters such as CaMV35S but there may be biochemical penalties in the plant resulting from increased starch deposition throughout the entire plant. Deposition in the endosperm is much preferred.

Possible promoters for use in the invention include the promoters of the starch synthase gene, ADPG pyrophosphorylase gene, and the sucrose synthase gene.

Branching enzyme vectors may be used to transform corn, with either constitutive or endosperm-specific promoters. The transit peptides from corn amyloplast-specific enzymes may be incorporated to direct the product to the plastid.

EFFECTS ON STARCH FINE STRUCTURE

Although this invention is directed primarily to improvement of the deposition of starch at elevated climatic temperatures, alteration of starch deposition inevitably leads to alteration of starch fine structure.

In cereal crops, changing the ratios and activities of SSS and BE and/or the source of the enzymes (eg replacing maize SSS with pea SSS) alters the fine-branching structure of the starch. For example, the fine branching structure of starch is determined by the overall activities of the various isoforms of the SSS and BE enzymes being expressed during starch deposition in the developing endosperm. Altering the ratios of these isoforms may be achieved by transformation techniques in which some of the natural enzyme activities are repressed whilst others are over-expressed in a manner analogous to the changes reported herein for the starch mutants of corn.

EFFECTS ON TEXTURE

Improved starch deposition also leads to alteration of the texture of crops such as tomatoes because increased amounts of starch in the fruit would increase the total solids content.

This effect would be significant in tomatoes which are grown for processing into paste. The quality of paste produced from processed tomatoes is in part related to the viscosity of the product which is usually determined by the Bostwick flow rate, reduced flow rate being desirable. The factors that interact to give a thicker product with reduced flow rate are complex, involving interactions between insoluble and soluble components. It is important to note that the characteristics of components in whole fruit will change during processing because of enzyme action and chemical changes brought about by heating which is involved in tomato processing by the so-called "hot-break" method.

The consistency of hot break paste is likely to be improved by increasing the level of insoluble solids in the whole fruit used in processing. Increased levels of soluble and insoluble solids in processing tomatoes has been an object of plant breeders for many years.

Soluble solids are the solutes in the tomato serum and consists primarily of carbohydrates. Paste is normally sold on the basis of its natural tomato soluble solids (NTSS) content. Because the sugars are the major contributors to NTSS, a higher sugar content contributes to a higher yield of paste per tonne of tomatoes. The correlation between NTSS and total solids (TS) is very high, although the relationship varies amongst tomato cultivars. High NTSS levels in ripe fruit may be an indirect measure of the starch component of the insoluble solids during fruit development. Sugar content is a critical component of the flavour of tomatoes.

Insoluble solids (IS) consist mainly of the polysaccharides in the cell wall. Residual starch will also contribute to the IS although, in normal ripening, this forms a small component. The IS/TS ratio partially determines the consistency of tomato products. Where high consistency is required, a greater quantity of IS improves the product quality. IS are measured as both water-insoluble solids (WIS) and alcohol-insoluble solids (AIS), the AIS quantities are greater than those for WIS because smaller polysaccharides are less soluble in 80% ethanol than in water.

It is believed that, by the method of this invention, the increased amounts of starch may very well accumulate in plastid granules and are, therefore, unlikely to contribute much to improved consistency. However, the heating involved in the hot break process and in the concentration step of hot and cold break products is likely to burst the granules and partially solubilise the starch, resulting in increased viscosity.

Enhanced starch synthesis is also likely to elevate the import of carbohydrate into the fruit which may also result in enhanced levels of soluble solids in the ripe fruit. This may also be considered as advantageous in fruit intended for the fresh fruit market.

In summary, then, improved insoluble solids leads to improved consistency of paste and higher yields of paste per tonne of tomato processed, whereas increased soluble solids will result in higher yields of paste per tonne of tomato processed and improved sugar component of flavour.

In tomato, the free sugars are almost entirely fructose and glucose. Sucrose is present but rarely exceeds 1% of the dry weight. Starch and structural polysaccharides are the major forms of storage of imported carbon. Starch levels increase in the early stages of fruit development, followed by a decrease to virtually zero by ripeness. Thus, in ripe fruit, hexoses (glucose and fructose) are the primary component of the soluble solids and account for about 50% of the fruit dry weight.

Thus, from the known facts about the ripening process it is believed that increasing the soluble solids is advantageous and that this increase may be obtained by transformation with a gene encoding glycogen synthase.

Our invention is thus applicable to plants whose value is due to the texture and/or sweetness and/or taste of the fruit. For example fruits such as tomato, melon, peach, pear, etc where the accumulation of starch is an early event in fruit development but is later degraded during fruit ripening releasing sugars. In this case the desirable trait is extra starch deposition which is useful in providing enhanced fruit texture and sweetness as well as increased thickening quality during cooking (eg, during ketchup/catsup manufacture from tomato).

OTHER USEFUL EFFECTS

Starch deposition in the developing pollen grains of cereals is an essential prerequisite for pollen viability. If starch synthesis is impaired by high temperatures in the developing pollen cells, reduced pollen viability will result. The insertion, according to the invention, of thermally stable variants of the SSS and/or BE and/or GS enzyme genes into cereal pollen increases pollen viability and seed set is less impaired by exposure to high temperatures.

Starch synthesis in leaf chloroplasts is also limited by the thermal lability of the SSS and BE enzymes. Photosynthetic rates in green leaf tissue are dependent in part on the ability of the cells to convert fixed carbon into starch and sucrose. When starch synthesis becomes limited at high temperatures because of rate limitation by SSS or BE, there is an accumulation of metabolic intermediates in the chloroplast, causing feedback inhibition of ribulose bisphosphate regeneration, reducing the overall carbon fixation by photosynthesis. Insertion of thermally stable variants of the enzymes, or additional copies of the relevant gene(s), increases the photosynthetic rate at high temperatures. This will increase the yield of all crops whose yield is dependent on the photosynthetic rate of the source leaves during at least a part of their life cycle. Examples include cereal crops such as maize, sorghum, wheat, barley and rice; root crops such as potato, turnip, yam and cassava; sugar crops such as beet and cane; oilseed crops such as rapeseed, sunflower, oil palm, coconut, linseed and groundnut; fruits such as apples, pears and bananas; and meal crops such as soya, beans and peas. The yields of all of these crops may be limited by source activity at particular times in their life cycle.

Our invention is also applicable to plants whose yield depends on gross biomass accumulation and which are limited by photosynthetic rate. Examples are forage crops such as grasses, ryegrass, forage maize and alfalfa; trees grown for wood, pulp or ethanol production and vegetables such as cauliflower, cabbage and sprouts.

CROSS-BREEDING

In one specific aspect, our invention is a method of producing a novel substantially homozygous maize (corn) line having superior starch deposition properties which comprises, (i) identifying a range of potential donor plants which are sexually compatible with a recipient maize plant and screening producing soluble starch synthase (SSS) enzyme or branching enzyme (BE) to determine the heat stability of the reaction of at least one of said enzymes; (ii) identifying a plant producing an enhanced SSS or BE enzyme that is significantly more heat-stable for the enzyme reaction than the corresponding enzyme in the recipient maize plant; (iii) crossing the identified plant with the recipient maize plant; (iv) selecting from among the progeny those expressing the heat stable enzyme reaction of the donor; and, (v) breeding therefrom so as to produce a novel substantially homozygous maize line having an enhanced rate of starch deposition.

Genotypes with a measurable enhancement in SSS or BE activity or altered characteristics with respect to temperature, are introduced into a back-crossing programme with a commercial maize inbred. Progeny are selected on the basis of genetic similarity to the commercial line, using RFLP's (restriction fragment length polymorphisms), but with the desired SSS or BE characteristics. Selected progeny are entered into further back-crossing against the commercial line. The end result is a new maize inbred line, genetically vary similar to the parental line, having enhanced SSS or BE activity. The temperature optimum of starch synthesis is measured before including the new line in hybrid production.

Another embodiment of our invention is a method of producing a novel substantially homozygous maize (corn) line having superior starch deposition properties which comprises, (i) identifying a range of potential donor plants which are sexually compatible with a recipient maize plant and screening for plants with high rates of grain starch synthesis at elevated temperatures; (ii) identifying a plant producing an enhanced rate of starch deposition that is significantly more heat-stable than the corresponding rate in the recipient maize plant; (iii) crossing the identified plant with the recipient maize plant; (iv) selecting from among the progeny those expressing the high rate of starch deposition; and, (v) breeding therefrom so as to produce a novel substantially homozygous maize line having an enhanced rate of starch deposition.

Genotypes with a measurable enhancement in starch deposition rates with respect to temperature are introduced into a back-crossing programme with a commercial maize inbred. Progeny are selected on the basis of genetic similarity to the commercial line, using RFLP's (restriction fragment length polymorphisms), but with the desired SSS or BE characteristics. Selected progeny are entered into further back-crossing against the commercial line. The end result is a new maize inbred line, genetically vary similar to the parental line, having enhanced SSS or BE activity. The temperature optimum of starch synthesis is measured before including the new line in hybrid production.

EXAMPLE 1

Sexual Crossing

The plants selected for screening were maize plants: either commercial maize varieties or varieties from more exotic collections. The material selected for screening was from amongst other Zea germplasm, for example, *Zea tripsacum, perennis, diploperennis, luxurians, parviglumis, mexicana* and *mays*. Many thousands of potential donors exist throughout the world where maze is grown as a cultivated crop or where it exists in the wild plant population, for example in South and Central America and Africa. Most of the Zea family can be inter-bred by traditional plant breeding methods.

Figure 20:
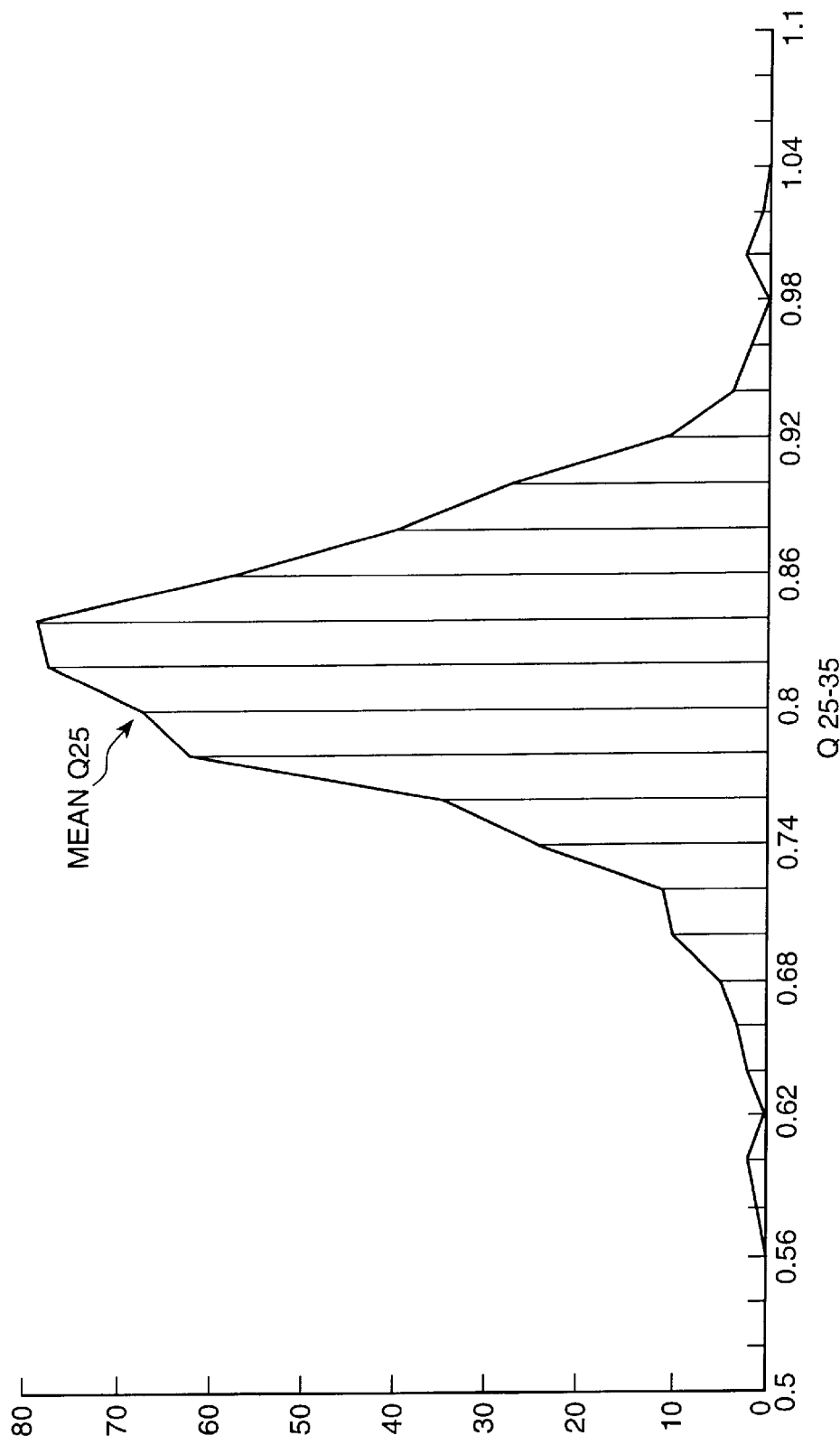
FIG. 20 is a graph showing the frequency distribution for $Q_{10}$ values (25 to 35° C.) for different maize lines.

One characteristic sought for use in this invention was an increase (or minimal loss) in activity from 25 to 35° C. A $Q_{10}$ value for each line was obtained by a method which is hereinafter described. The frequency distribution for all the germplasm assayed in the screen (FIG. 20) shows that the range of variation for this trait is quite narrow. However, our screen succeeded in locating a few rare occurrences from the extremely wide selection of Zea germplasm. Across all the germplasm the overall average drop in activity between 25 and 35° C. was around 40% ($Q_{10}$=0.61) with a range of 65% to 0% drop in activity ($Q_{10}$ range of 0.35 to 1.00). A selection of sixteen inbreds used in commercial hybrids showed a narrower range of 41% to 20% drop in activity ($Q_{10}$ of from 0.59 to 0.80 with an average of 0.70) indicating that conventional maize breeding which involves selection of yield-for-moisture may possibly have been effective in weeding-out the very worst forms of the enzyme. However, there is clearly room for further improvement in several inbreds and hence it is possible to gain potential yield benefit in commercial hybrids.

Figure 21:
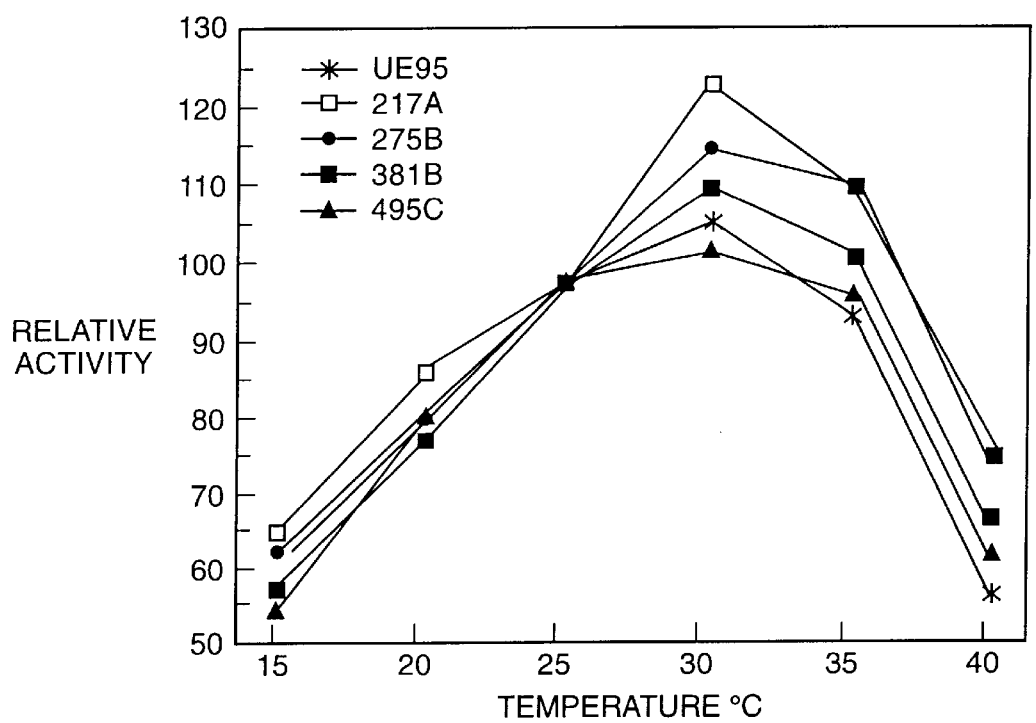
FIG. 21 is a graph showing soluble starch synthase activity against temperature for various maize genotypes.

The very best forms of SSS identified (from a screen of nearly 1,000 sources of Zea germplasm) were in 4 exotic lines from Peru (Lima 38 and Lima 45) and Mexico (Guanajuato 13) and teosinte with Q10 as high as 1.0. Three of these lines were obtained from the Plant Introduction Centre, Iowa State University: Numbers P1515021, Ames 8545, PI490879 and one teosinte line obtained from Dr John Deobley *Zea mays* subsp. Mexicana, Doebley 479. The temperature/activity profiles (FIG. 21) of these forms of the enzyme(s) show a dramatic difference from one commercially valuable inbred line (UE95) which was included for comparison.

These two exotic lines have been crossed into commercial inbred germplasm to produce $F_1$ hybrids.

GENE MANIPULATION

A donor gene may also be introduced into a recipient plant by transformation.

When genetic manipulation techniques are employed in this invention there are at least four possibilities:

(1) Increase the amount and activities of the enzyme SSS or BE or GS or any combination thereof in a recipient plant, such as a commercial maize line or population by the insertion of extra gene copies of the SSS, BE or GS enzymes. The source of these extra copies may be the recipient line itself as the technique would simply increase the amount of enzyme available in the grain rather than the changing of the properties of the enzyme (s). The gene promoters and other regulatory sequences may also be altered to achieve increased amounts of the enzyme in the recipient plant.

(2) The insertion of a gene or genes specifying SSS and/or BE and/or GS enzymes with activities which increase with temperature up to 30° C. Achieving this requires the identification of a source of the thermally stable enzyme gene. However, the use of genetic manipulation techniques for introduction of the new genes places no restriction of the source to sexually compatible species and genetic material may be obtained from any source of the SSS, BE and GS enzymes having the desired temperature/activity characteristics. Enzymes from plant species other than cereals, particularly plants which grow well in tropical or sub-tropical regions will most likely exhibit greater temperature stability in the SSS and BE enzymes than maize. The exogenous genetic material may altered by genetic engineering to give the desired characteristics to the enzymes. Techniques are known in so-called "protein engineering" which can alter the characteristics of an enzyme.

(3) Change the ratios of activities of the isoforms of enzymes SSS or BE or any combination thereof in a recipient plant, such as a commercial maize line or population by the insertion of extra gene copies of the SSS, BE enzymes and/or by insertion of anti-sense gene constructs. The source of these extra copies or antisense constructs may be the recipient line itself as the technique would simply increase or decrease the amount of enzyme available in the grain rather than the changing of the properties of the enzyme(s). The gene promoters and other regulatory sequences may also be altered to achieve increased amounts of the enzyme in the recipient plant.

(4) The insertion of a gene or genes specifying SSS and/or BE and/or GS enzymes with activities which effect a change in the fine structure of the starch. Achieving this requires the identification of a source of the enzyme gene. However, the use of genetic manipulation techniques for introduction of the new genes places no restriction of the source to sexually compatible species and genetic material may be obtained from any source of the SSS, BE and GS enzymes having the desired characteristics. Enzymes from plant species other than cereals, particularly plants which grow well in tropical or sub-tropical regions will most likely exhibit altered starch specificities in the SSS and BE enzymes than maize. The exogenous genetic material may altered by genetic engineering to give the desired characteristics to the enzymes. Techniques are known in so-called "protein engineering" which can alter the characteristics of an enzyme.

ISOLATION OF A DONOR GENE

The donor gene may be isolated from a suitable biological organism (including plants, fungi, bacteria or animal cells) after screening a range of potential donor organisms producing soluble starch synthase (SSS) enzyme, glycogen synthase (GS) or branching enzyme (BE) to determine the heat stability of the reaction of at least one of said enzymes. (In bacteria or animals, glycogen is deposited rather than starch and so these organisms contain glycogen synthases and branching enzymes).

EXAMPLE 2

Screening for Source Material

We have devised a means (an enzyme-activity based screen) of identifying heat-stable forms of the enzymes. When the natural *Zea mays* temperature sensitive enzymes are replaced with temperature stable enzymes from another organism, provided the replacement enzymes are not disrupted by low temperatures in the environment, maize plants with higher rates of starch synthesis at temperatures above 25° C. will result.

The screen used in this invention identified enzyme forms with increased (or minimal loss in activity from 25 to 35° C. However, the characteristics sought for use in the invention can be any one, or several in combination, of the following characteristics:

(1) a high increase in activity between 20 and 25° C.;

(2) increased (or minimal loss in) activity from 25 to 30° C.;

(3) increased (or minimal loss in) activity from 30 to 35° C.;

(4) increased stability to "knockdown", where knockdown is defined as an irreversible loss in activity caused by elevated temperatures; and, (5) instrinsically high activity at 20° C.

EXAMPLE 3

Enzyme Activity Assay

In order to assess the suitability of the native enzymes of potential gene donor plants, it is necessary to be able to assay for the thermally stable enzymes. We have devised the following procedure.

1. Homogenise grain or endosperm tissue and extract protein into a buffer solution which maintains the SSS and BE enzymes in an active form.

2. Assay SSS activity by adding 50 $\mu$l of the enzyme extract to 25 $\mu$l of primer (glycogen, amylopectin, starch) and 100 $\mu$l of a buffer solution of the following final concentrations: 100 mM bicine, 25 mM potassium chloride, 5 mM EDTA, and 10 mM reduced glutathione.

3. Begin the assay by adding $^{14}$C-ADP-glucose. Stop the assay after a defined time at a defined temperature by adding 1 ml of 0.1M sodium hydroxide. Precipitate the primer by bringing the mixture to 75% methanol concentration. Centrifuge and recover the primer pellet and redissolve in sodium hydroxide and reprecipitate in 75% methanol. Repeat the repreciptation procedure.

4. Following the second wash, dissolve the primer in 1M hydrochloric acid at 100° C. Cool and add the mixture to scintillation fluid and measure the $^{14}$C-ADP-glucose transferred to the primer.

5. BE activity is assayed by adding 50 $\mu$l of the enzyme extract to a mixture containing citrate buffer, AMP, and phosphorylase A.

6. Start the reaction by adding an aliquot of $^{14}$C-glucose-1-phosphate. Stop the reaction after a defined time at a selected temperature by adding 0.1M sodium hydroxide.

7. Add a polysaccharide (amylose, glycogen, amylopectin, starch) as a carrier and precipitate the polysaccharide with 75% methanol. Centrifuge and wash the polysaccharide precipitate and dissolve and count the scintillation as described in step 4 above. BE activity is defined as the stimulation achieved by the enzyme in the incorporation of $^{14}$C-glucose from the glucose-1-phosphate into the polysaccharide by the phosphorylase A.

EXAMPLE 4

Isolation of Soluble Starch Synthase (SSS) and Branching Enzyme (BE) Genes

Using standard cloning techniques, the SSS and BE genes may be isolated.

The source of the genes was a US sweet-corn line of Zea mays, from which the enzyme protein was purified. Endosperms from the maize line were homogenised in a buffer which maintains the SSS and BE in active form. The enzymes were partially purified by ammonium sulphate fractionation, followed by DEAE Sepharose chromatography, followed by FPLC using a Superose gel filtration column, followed by FPLC using a Mono Q anion exchange column. The Superose column allows separation of SSS from BE activity. Further purification of individual isoforms was achieved by hydroxyapatite, cation exchange FPLC or isochromatofocussing.

Purification of the SSS from maize (Silver Queen) has been achieved (Wasserman etal) by a combination of ammonium sulphate precipitation, ion exchange chromatography, affinity chromatography (Affi-Gel Blue) and two FPLC steps, Mono-Q and Superose-12. This results in up to 5,000-fold purification with yields up to 5%. The SSS polypeptide was a single subunit of molecular weight 86 kD. Other SSS polypeptides were present in a US dent inbred line at around 70 kD and 105 kD molecular weight.

Ammonium sulphate precipitation of SSS I is best achieved using 40% ammonium sulphate which produces a translucent SSS-enriched pellet which is next dialysed and further fractionated using DEAE-cellulose ion-exchange chromatography. These steps increase specific activities by up to 50-fold. The affinity chromatography steps rely on the ADP attached to a Sepharose matrix either through the N-amino group or through The ribose hydroxyl group. SSS I is readily eluted with 2 mM ADP at pH 8.5. Specific activities are increased by up to 10-fold using the affinity chromatography step with a yield of around 15%. SSS is next purified by Mono-Q FPLC steps with elution of activity at low potassium chloride (not more than 200 mM KCl).

Figure 22:
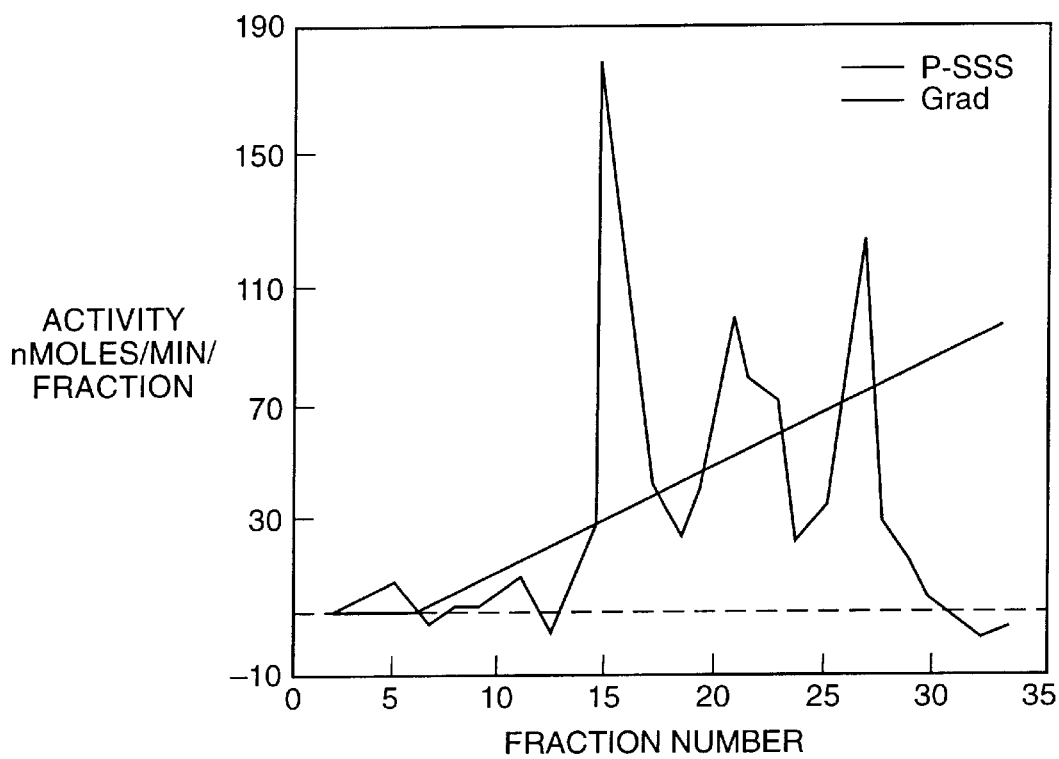
FIG. 22 is a graph showing soluble starch synthase activity eluted from the mono-Q column.

Purification of the SSS and BE enzymes from the US inbred line identified three SSS and three BE isoforms. FIG. 22 shows the data for SSS; BE behaves similarly. Preliminary investigations have suggested that these isoforms have slightly different temperature optima of activity and also slightly different temperature thresholds for knockdown.

In the final purification step the SSS or BE preparations were loaded on to SDS PAGE gels. The bands corresponding to the SSS or BE polypeptides were cut out and eluted. The pure polypeptide was then used as an antigen to generate polyclonal antibodies in a rabbit. The antibodies were then tested for specificity to the SSS or BE polypeptides. N-terminal amino acid sequences were also obtained from the polypeptides.

Full sequencing of the maize polypeptides is continuing. Amino acid sequencing of the maize SSS polypeptide has provisionally yielded the following partial sequence: Ala-Ala-xxx-Arg-Lys-Ala-Val-Met-Val-Pro-xxx-Gly-xxx-Asn-Arg-Glu-Phe-Val-Lys-Tyr-Leu-Phe-xxx-Met/Phe-Ala-Gln (SEQ ID NO:9). The final sequence may be compared to the amino acid sequence of pea SSS I and SSS II published by Dry et al (1991, Plant Journal, 2:193–202).

The antibodies may be used to screen a maize endosperm cDNA library for clones derived from the mRNAs for SSS or BE in an in vitro transcription/translation system.

The cDNAS thus derived may be used to probe a maize genomic library and the maize SSS and BE genomic DNAs may be isolated. In addition N-terminal amino acid sequence information for SSS and BE may be used to generate oligonucleotide probes. These probes may be used to screen the maize genomic library and the maize SSS and BE genomic DNAs may be isolated.

TRANSFORMATION (i) Insertion of Extra Copies of the Gene

Maize genomic DNAs isolated as above may subsequently be transformed into either protoplasts or other tissues of a maize inbred line or population. The existing gene promoters ensure that the extra genes are expressed only in the developing endosperm at the correct developmental time. The protein sequences likewise ensure that the enzymes are inserted into the amyloplast.

Transgenic maize plants are regenerated and the endosperms of these plants are tested for increased SSS and BE enzyme activity. The kernels are also tested for enhanced rate of starch synthesis at different temperatures. The plants are then included in a breeding programme to produce new maize hybrids with higher rates of starch synthesis at temperatures above the normal optimum.

(ii) Insertion of Genes Specifying SSS and/or BE with Higher Temperature Optima for Activity.

This is also achieved by standard cloning techniques. The source of the temperature-stable forms of the SSS or BE or GS genes is any organism that can make starch or glycogen. Potential donor organisms are screened and identified as described above. Thereafter there are two approaches: (a) via enzyme purification and antibody/sequence generation using the protocol described above. (b) using SSS and BE and GS cDNAs as heterologous probes to identify the genomic DNAs for SSS and BE and GS in libraries from the organism concerned. The gene transformation, plant regeneration and testing protocols are as described above. In this instance it is necessary to make gene constructs for transformation which contain the regulatory sequences from maize endosperm SSS or BE or another maize endosperm starch synthesis pathway enzyme to ensure expression in endosperm at the correct developmental time (eg, ADPG pyrophosphorylase).

One specific example of this is with the bacterial glycogen synthase enzyme which we have found to be essentially tolerant of temperatures up to 40° C. The nucleotide and amino-acid sequences of glycogen synthase are known (i) from E Coli GenBank/EMBL #JO2616 (Kumar et al, J Biol Chem 34 16256–16259 (1986)). (ii) from rabbit skeletal muscle (Zhang et al, FASEB J 3 2532–2536 1989)), and (iii) from human muscle (Browner et al, Proc Nat Acad 5cl 86 1443–1447 (1989)). Gene constructs used to transform plants requires the regulatory sequences from maize endosperm SSS or BE or another maize endosperm starch synthesis pathway enzyme to ensure expression in endosperm at the correct development time (eg, ADPG pyrophosphorylase). Furthermore the gene constructs also requires a suitable amyloplast transit-peptide sequence such as from maize endosperm SSS or BE or another maize endosperm starch synthesis pathway enzyme to censure expression of the amyloplast at the correct developmental time (eg, ADPG pyrophosphorylase).

Genetic protein engineering techniques may also be used to alter the amino acid sequence of the SSS or BE or GS enzymes to impart higher temperature optima for activity. The genes for SSS and/or BE and/or GS may be cloned into a bacteria which relies on these enzymes for survival. Selection for bacteria surviving at evaluated temperatures enables the isolation of mutated thermostable enzyme forms. Transformation of maize with the altered genes is carried out as described above.

Genetic protein engineering techniques may also be used to alter the amino acid sequence of the maize SSS or BE enzymes to impart higher temperature optima for activity. The genes for SSS and/or BE may be cloned into bacteria relies on the these enzymes for survival. Selection for bacteria surviving at elevated temperatures enables the isolation of mutated thermostable enzymes forms. Transformation of maize with the altered genes is carried out as described above.

(iii) Changing the Ratios of Activities of the Isoforms of Enzymes SSS or BE.

This is also achieved by standard cloning techniques. The source of the SSS or BE genes is maize using the protocol described above. Plants are then transformed by insertion of extra gene copies of the isoforms of SSS, BE enzymes and/or by insertion of anti-sense gene constructs. The gene promoters and other regulatory sequences may also be altered to achieve increased amounts of the enzyme in the recipient plant.

(iv) Insertion of a Gene or Genes Specifying SSS and/or BE and/or GS Enzymes with Activities which Effect a Change in the Fine Structure of the Starch.

This is also achieved by standard cloning techniques. The source of the special forms of the SSS or BE or GS genes is any organism that can make starch or glycogen. Potential donor organisms are screened and identified as described above. Thereafter there are two approaches:

(a) via enzyme purification and antibody/sequence generation using the protocol described above.
(b) using SSS and BE and GS cDNAs as heterologous probes to identify the genomic DNAs for SSS and BE and GS in libraries from the organism concerned. The gene transformation, plant regeneration and testing protocols are as described above. In this instance it is necessary to make gene constructs for transformation which contain the regulatory sequences from maize endosperm SSS or BE or another maize endosperm starch synthesis pathway enzyme to ensure expression in endosperm at the correct developmental time (eg, ADPG pyrophosphorylase).

We claim:

1. A method of producing a cereal plant comprising stably incorporating into the genome of a recipient cereal plant one or more donor genes encoding an enzyme involved in a starch or glycogen biosynthetic pathway, said enzyme having a higher temperature optimum during the grain-filling period than an equivalent enzyme in said recipient cereal plant, thereby producing a cereal plant with an increased temperature optimum for starch synthesis as compared to the recipient cereal plant; wherein the donor gene encodes soluble starch synthase, branching enzyme or an animal or fungal glycogen synthase.

2. A method as claimed in claim 1 in which the plant has an improved capacity to produce starch at elevated temperature.

3. A method as claimed in claim 1 in which the plant has an ability to synthesise starch with an altered fine structure.

4. A method as claimed in claim 1 in which at least one of the donor genes is from a plant.

5. A method as claimed in claim 4 in which the donor gene is from a plant of the species *Zea mays, Zea diploperennis, Zea luxurians, Zea perennis, Zea tripsacum, Zea parviglumis, Zea mexicana* or teosinte.

6. A method as claimed in claim 5 in which the donor gene is from a plant of the *Zea mays* varieties Lima 38, Guanajuato 13, Lima 45, Doebley 479 or teosinte 154.

7. A method as claimed in claim 1 in which at least one of the donor genes is from a bacterium.

8. A method as claimed in claim 1 in which at least one of the donor genes is from a fungus.

9. A method as claimed in claim 1 in which at least one of the donor genes is from an animal cell.

10. A method as claimed in claim 1 in which at least one of the donor genes specifies a modified allelic form of the enzyme.

11. A method as claimed in claim 1 in which at least one of the donor genes is derived from a sexually compatible donor plant and is inserted into the recipient plant by sexual crossing of donor and recipient plants.

12. A method as claimed in claim 1 in which at least one of the donor genes is incorporated into the recipient genome by genetic transformation.

13. A method as claimed in claim 1 in which the recipient plant is of the species *Zea mays*.

14. A method as claimed in claim 1, in which at least one donor gene encodes glycogen synthase from an animal.

15. A method of producing a maize plant with increased temperature optimum for starch synthesis, comprising stably incorporating one or more donor genes encoding an enzyme involved in a starch or glycogen biosynthetic pathway into a recipient maize plant genome, said enzyme having a higher temperature optimum during the grain-filling period than an equivalent enzyme in said recipient maize plant, thereby producing the maize plant with increased temperature optimum for starch synthesis as compared to the recipient maize plant; wherein the donor gene encodes soluble starch synthase, branching enzyme or an animal or fungal glycogen synthase.

16. A method according to claim 1 wherein said cereal plant is selected from the group consisting of maize, wheat, rice, sorghum and millet.

* * * * *

SEQUENCE LISTING

<160> NUMBER OF SEQ ID NOS: 9

<210> SEQ ID NO 1
<211> LENGTH: 1601
<212> TYPE: DNA
<213> ORGANISM: Escherichia coli

<400> SEQUENCE: 1

```
gtgattggtg aaaacgcaga ggaagatgca cgtcgtttct atcgttcaga agaaggcatc        60
gtgctggtaa cgcgcgaaat gctacggaag ttagggcata aacaggagcg ataatgcagg       120
ttttacatgt atgttcagag atgttcccgc tgcttaaaac cggcggtctg gctgatgtta       180
ttggggcatt acccgcagca caaatcgcag acggcgttga cgctcgcgta ctgttgcctg       240
catttcccga cattcgccgt ggcgtgaccg atgcgcaggt agtatcccgt cgtgatacct       300
ccgccggaca tatcacgctg ttgttcggtc attacaacgg ggttggcatt tacctgattg       360
acgcgccgca tctctatgat cgtccgggaa gtccgtatca cgataccaac ttatttgtcc       420
ataccgacaa cgtattgcgt tttgcgctgc tggggtgggt tggggcagaa atggccagcg       480
ggcttgaccc attctggcgt cctgatgtgg tgcatgcgca cgactggcat gcaggccttg       540
cgcctgcgta tctggcggcg cgcgggcgtc cggcgaagtc ggtgtttact gtgcacaacc       600
tagcctatca aggcatgttt tatgcacatc acatgaatga catccaattg ccatggtcat       660
tctttaatat tcatgggctg gaattcaacg gacaaatctc tttcctgaag gccggtctgt       720
actatgccga tcacattacg gcggtcagtc caacctacg tcgcgagatc accgaaccgc       780
agtttgccta cggtatggaa ggtctgttgc aacagcgtca ccgcgaaggg cgtcttccg        840 gcgtaccgaa cggcgtggac gagaaaatct ggagtccaga gacggactta ctgttggcct       900
cgcgttacac ccgcgatacg ttggaagata agcggaaaa taagcgccag tcacaaatcg       960
caatgggatc caaggttgac gataaagtgc cgcttttttgc agtggtgagc cgtctgacca     1020
gccagaaagg tctcgattcg gtgctggaag cctcaccggg ttcttcggag cagggcgggc     1080
```

-continued

```
agctggcgct actcggcgcg ggcgatccgg tgctgcagga aggtttcctt gcggcggcag    1140
cggaataccc cggtcaggtg ggcgttcaga ttggctatca cgaagcattt tcgcatcgca    1200
ttatgggcgg cgcggacgtc attctggtgc ccagccgttt cgaaccgtgc ggcttaacgc    1260
aactttatgg atcgaagtac ggtacgctgc cgttagtgcg acgcaccggt gggcttgctg    1320
atacggtttc tgactgttct ctcgagaacc ttgcagatgg cgtcgccaat gggtttatct    1380
tcgaagatag taatgcctgg tcgctgttac ggactattcg acgtgctttt gtactgtggt    1440
cctgtcctcc actgtggcgg tttgtgcaac gtcaggctat gcaatggat tttggctggc     1500 aggtcgcggc gaagtcgtac cgtgagcttt actatcgctc gaaatagttt tcaggaaacg    1560
cctacatgaa tgctccgttt acatattcat cgcccacgct t                        1601
```

```
<210> SEQ ID NO 2
<211> LENGTH: 10
<212> TYPE: DNA
<213> ORGANISM: Escherichia coli

<400> SEQUENCE: 2
gataatgcag                                                             10

<210> SEQ ID NO 3
<211> LENGTH: 10
<212> TYPE: DNA
<213> ORGANISM: Maize

<400> SEQUENCE: 3
aacaatggct                                                             10

<210> SEQ ID NO 4
<211> LENGTH: 56
<212> TYPE: PRT
<213> ORGANISM: RUBISCO transit peptide consensus sequence

<400> SEQUENCE: 4

Met Ala Ser Ser Met Leu Ser Ser Ala Ala Val Ala Thr Arg Thr Asn
  1               5                  10                  15

Pro Ala Gln Ala Ser Met Val Ala Pro Phe Thr Gly Leu Lys Ser Ala
                 20                  25                  30

Ala Phe Pro Val Ser Arg Lys Gln Asn Leu Asp Ile Thr Ser Ile Ala
             35                  40                  45

Ser Asn Gly Gly Arg Val Gln Cys
         50                  55

<210> SEQ ID NO 5
<211> LENGTH: 58
<212> TYPE: PRT
<213> ORGANISM: Corn

<400> SEQUENCE: 5

Met Ala Pro Thr Val Met Met Ala Ser Ser Ala Thr Ala Thr Arg Thr
  1               5                  10                  15

Asn Pro Ala Gln Ala Ser Ala Val Ala Pro Phe Gln Gly Leu Lys Ser
                 20                  25                  30

Thr Ala Ser Leu Pro Val Ala Arg Arg Ser Ser Arg Ser Leu Gly Asn
             35                  40                  45

Val Ala Ser Asn Gly Gly Arg Ile Arg Cys
         50                  55
```

-continued

```
<210> SEQ ID NO 6
<211> LENGTH: 73
<212> TYPE: PRT
<213> ORGANISM: Corn

<400> SEQUENCE: 6

Met Ala Ala Leu Ala Thr Ser Gln Leu Val Ala Thr Arg Ala Gly Leu
  1               5                  10                  15

Gly Val Pro Asp Ala Ser Thr Phe Arg Arg Gly Ala Ala Gln Gly Leu
             20                  25                  30

Arg Gly Ala Arg Ala Ser Ala Ala Asp Thr Leu Ser Met Arg Thr
         35                  40                  45

Ala Ser Ala Arg Ala Ala Pro Arg His Gln Gln Ala Arg Gly
 50                  55                  60

Gly Arg Phe Pro Ser Leu Val Val Cys
 65                  70

<210> SEQ ID NO 7
<211> LENGTH: 58
<212> TYPE: PRT
<213> ORGANISM: Corn

<400> SEQUENCE: 7

Met Ala Gln Ile Leu Ala Pro Ser Thr Gln Trp Gln Met Arg Ile Thr
  1               5                  10                  15

Lys Thr Ser Pro Cys Ala Thr Pro Ile Thr Ser Lys Met Trp Ser Ser
             20                  25                  30

Leu Val Met Lys Gln Thr Lys Lys Val Ala His Ser Ala Lys Phe Arg
         35                  40                  45

Val Met Ala Val Asn Ser Glu Asn Gly Thr
 50                  55

<210> SEQ ID NO 8
<211> LENGTH: 33
<212> TYPE: PRT
<213> ORGANISM: Wheat

<400> SEQUENCE: 8

Arg Ala Ser Pro Pro Ser Glu Ser Arg Ala Pro Leu Arg Ala Pro Gln
  1               5                  10                  15

Arg Ser Ala Thr Arg Gln His Gln Ala Arg Gln Gly Pro Arg Arg Met
             20                  25                  30

Cys

<210> SEQ ID NO 9
<211> LENGTH: 26
<212> TYPE: PRT
<213> ORGANISM: Maize
<220> FEATURE:
<221> NAME/KEY: UNSURE
<222> LOCATION: (3)..(24)
<223> OTHER INFORMATION: Residues 3, 11, 13 and 23 are undetermined;
      residue 24 could be Met or Phe.

<400> SEQUENCE: 9

Ala Ala Xaa Arg Lys Ala Val Met Val Pro Xaa Gly Xaa Asn Arg Glu
  1               5                  10                  15

Phe Val Lys Tyr Leu Phe Xaa Xaa Ala Gln
             20                  25
```